US006194145B1

(12) United States Patent
Heidrich et al.

(10) Patent No.: US 6,194,145 B1
(45) **Date of Patent: *Feb. 27, 2001**

(54) GENUS AND SPECIES-SPECIFIC IDENTIFICATION OF LEGIONELLA

(75) Inventors: Björn Heidrich; Peter-Nicholas Robinson; Frank Tiecke, all of Berlin; Arndt Rolfs, Rostock, all of (DE)

(73) Assignee: Roche Diagnostics GmbH, Mannheim (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/638,931

(22) Filed: Apr. 25, 1996

(30) Foreign Application Priority Data

Apr. 29, 1995 (DE) .............................................. 195 15 891

(51) Int. Cl.[7] ............................ C12Q 1/68; C07H 21/02; C07H 21/04; C12P 19/34

(52) U.S. Cl. ............................ 435/6; 536/23.1; 536/24.3; 435/91.2

(58) Field of Search ..................... 435/6, 91.2; 536/23.1, 536/24.3

(56) References Cited

U.S. PATENT DOCUMENTS 5,273,883 * 12/1993 Saiki et al. ................................ 435/6
5,298,392 * 3/1994 Atlas et al. ............................ 435/600
5,427,930 * 6/1995 Birkenmeyer et al. ............. 435/91.2
5,491,225 * 2/1996 Picone et al. ...................... 536/24.32
5,569,586 * 10/1996 Pelletier et al. .......................... 435/6

FOREIGN PATENT DOCUMENTS

WO92/11273 * 7/1992 (WO) .
WO94/28174 * 12/1994 (WO) .

OTHER PUBLICATIONS

Landegrn et al., Science 241: 1077–1080 (1988).*

M. Maiwald, et al.; "Characterization of contaminating DNA in Taq polymerase which occurs during amplification with a primer set for Legionella 5S ribosomal RNA"; Molecular and Cellular Probes (1994) 8, pp. 11–14.*

P. Matsiota–Bernard, et al.; "Evaluation of Commercial Amplification Kit for Detection of *Legionella pneumophila* in Clinical Specimens", Journal of Clinical Microbiology, Jun. 1994, pp. 1503–1505.*

Robin K. Oshiro, et al., "Modification of reagents in the EnviroAmp™ kit to increase recovery of Legionella organisms in water", Canadian Journal of Microbiology, Jun. 1994, pp. 495–499.*

Harald H. Kessler, et al., "Rapid Detection of Legionella Species in Bronchoalveolar Lavage Fluids with the EnviroAmp Legionella PCR Amplification and Detection Kit", Journal of Clinical Microbiology, Dec. 1993, p. 3325–3328, vol. 31, No. 12.*

G. Lisby, et al.; "Construction of a DNA Amplification Assay for Detection of Legionella Species in Clinical Samples", Eur. J. Clin. Microbiol. Infect. Dis., Mar. 1994, p. 225–231, vol. 13, No. 3.*

Björn Heidrich, et al., "Automated Direct Sequencing Of Legionella 5S RDNA", Med. Microbiol. Lett. 1994; 3: 279–290.*

Mahbubani et al., Molecular and Cellular Probes 4: 175–187 (1990).*

MacDonell et al., Nucleic Acids Research 15(3): 1335 (1987).*

Grimont et al., Research in Microbiology 140: 615–626 (1989).*

Bangsborg et al., J. of Clinical Microbiology 33(2): 402–406 (Feb. 1995).*

Hookey et al., J. of Clinical Microbiology 33(9): 2377–2381 (Sep. 1995).*

Maiwald et al., Eur. J. of Clinical Microbiology and Infectious Diseases 14(1): 25–33 (1995).*

Klin. Lab. 1994; 40: 211–216 (Heidrich et al.).*

* cited by examiner

*Primary Examiner*—W. Gary Jones
*Assistant Examiner*—Ethan Whisenant
(74) *Attorney, Agent, or Firm*—Nikaido Marmelstein Murray & Oram, LLP.

(57) ABSTRACT

Method for the genus-specific amplification of legionella and genus-specific or species-specific identification.

33 Claims, 5 Drawing Sheets

FIG. 1

```
1:   GCCTCCCTCAAGATGAGTTTTCCCATGAAGCCCGTTGAAGACTACGACGT

51:  TGATAGGCAAGGTGTGGAAGCGCAGTAATGCGTGAAGCTAACTTGTACTA

                                          23S/Spacer
101: ATTGGCTGATTGTCTTGACCATATAATCTGAGTGACTTCAGAA/TGTGATA

151: TTGATTTGTATACGTGAAACGTATCGTGTAAACTCTGACTCTTTACCAAA

                                          Spacer/5S
201: CCTGTGGCTTAATATAGCAATCAAAGCCTCAGGTAAACCAGTTT/TCCTGG

251  CGACTATAGCGATTTGGAACCACCTGATACCATCTCGAACTCAGAAGTGA

301: AACATTTCCGCGCCAATGATAGTGTGAGGCTTCCTC
```

GENUS AND SPECIES-SPECIFIC IDENTIFICATION OF LEGIONELLA

Subject matter of the invention is a method for amplifying nucleic acids of the genus legionella, and a method for the genus and species-specific detection of bacteria of the genus legionella and reagents suitable therefore.

Legionella are aquatic, ubiquitous gramnegative aerobic, facultatively intracellular rod-like bacteria. The legionellaceae family consists of a genus (legionella) and 48 currently known species and 51 sero groups. There exist 16 known serovars from the most important species L. pneumcphila. Their most important habitats include water pipes, air conditioning systems, and cooling towers. Infection of humans usually occurs via Legionella-containing aerosols. Legionellosis frequently occurs as an epidemic, e.g. via shower heads of warm-water systems, contaminated cooling water in air-conditioning system or sporadic. Person-to-person transmission has not yet been described.

Legionella infections can be divided in two groups: The legionnaires' disease, an acute severe pneumonia that is often accompanied by high fever, abdominal pain, headaches, myalgias, and confusion and other neurological symptoms; further, the Pontiac fever which is a self-limiting variant of legionellosis is accompanied by influenza-like symptoms.

The most important sero group of L. pneumophila is the L. pneumophila sero group 1 (L. pn. Sero. 1) which is the most frequently cause of the legionnaires' disease (approx. 80%). However, there exist great regional differences, especially when dealing- with nosocomially acquired legionellosis. As opposed thereto, L. micdadei and other non-pneumophila species have been described as the causative agent for Pontiac fever.

The diagnostical treatment of legionella is difficult. Legionella are difficult to dye with fuchsin, rendering a gram stain of the causative agent practically impossible. Legionella do not grow on commonly used culturing media, but only on special agars and at an atmosphere that contains 2.5–5% $CO_2$. The sensitivity of the culture is only approx. 20% for *L. pneumophila* and approx. 5% for other species.

For the detection of legionella, one has employed, inter alia, DNA-DNA hybridisation, Pulsfeld electrophoresis, ribotyping, restriction fragment length polymorphism, fatty acid and ubiquinone analysis, rRNA sequencing, RT-PCR and Southern blot, latex agglutination, Fourier-transformed infrared spectroscopy, indirect immunofluorescence and carbohydrate utilisation (BIOLOG system).

Med. Microbiol. Lett. 1994; 3: 279–290 and Clin. Lab. 1994; 40: 211–216 describe the sequencing of 5S-rDNA of legionella.

A kit for the detection of legionella in water samples is commercially available. The detection with the aid of this kit includes a first step where a fragment of the 5S-rDNA is genus-specifically amplified. A fragment of the MIP gene of the *L. pneumophila* species is amplified in the same vessel. The kit contains a total of seven primers for carrying out a multiplex PCR wherein two PCR amplificates are generated. Subsequently, the amplificates are detected via reverse dot blot. The necessity of great numbers of primers renders the method that is implemented with the aid of said kid rather complex as is its manufacture. Moreover, said method is unsatisfactory with respect to sensitivity.

It was, hence, an object of the present invention to provide reagents that facilitate the detection of legionella while comprising a smaller number of components. It was another object of invention to provide a more specific and potentially more variable legionella detection method.

BRIEF DESCRIPTION OF THE DRAWINGS

FIG. 1 shows an example of a nucleic acid sequence of the Legionella 23S-5S-spacer region.

Figure 2:
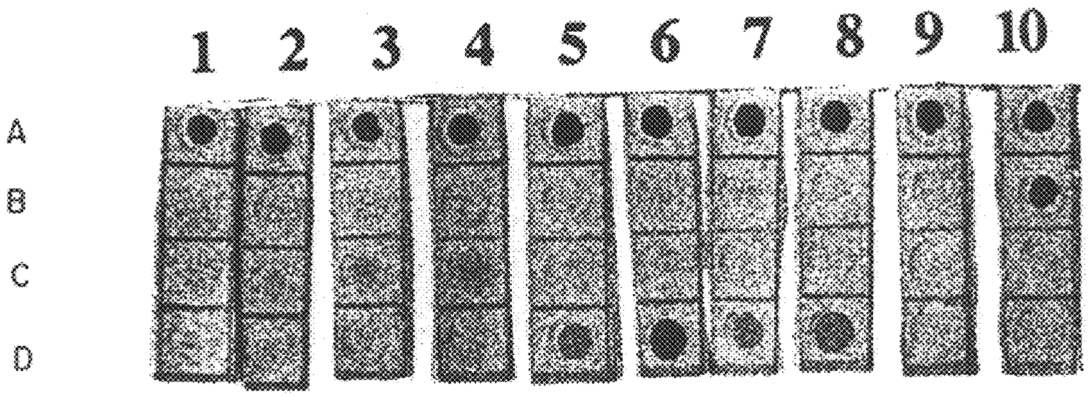
FIG. 2 shows the results obtained using reverse dot blotting.

Subject matter of the invention is, hence, in a first aspect a method of amplifying nucleic acids of the genus legionella, wherein nucleic acids of all possible species of the genus legionella are amplified with less than 7 primers. Another subject matter of invention is a method of detecting said bacteria with the aid of the aforementioned amplification method.

Another subject matter of the invention is a method of detecting bacteria of the genus legionella with the aid of a nucleic acid probe which comprises a sequence of at least 15 basis of length that exhibits at least 90% homology to a part of SEQ. ID. NO. 1 or which is at least 90% complementary to a part of SEQ. ID. NO. 1.

The core of the invention is to locate sequences on the legionella genome to allow generation of nucleic acid probes for the detection of all currently Known legionella species that are part of the genus legionella.

Amplification means an increase in the concentration of nucleic acids or parts thereof that are present in a reaction mixture. Examples for such amplification procedures are the polymerase chain reaction according to EP-B-0 201 184, the so-called NASBA method according to EP-A-0 329 822, and methods derived therefrom.

In the method described in EP-A-0 201 184. the nucleic acid to be amplified is present as a single strand or made available as a single strand with a molar excell of two oligonucleotide primers under hybridization conditions and in the presence of a polymerisation-inducing agent and nucleotides; the primers are selected such that, for each strand, an extension product of corresponding primers, which is complementary to the nucleic acid strand, is synthesized, and an extension product of a primer once separated from its complement, serves as a template for the synthesis of an extension product of the other primer. The extension products are then separated from the templates at which they were synthesized, and the so obtained extension products are used to again react with the primers. When these steps are repeated in cycles, it is theoretically possible to exponentially amplify a nucleic acid sequence which is within the outer hybridization position of the primer.

The method of EP-A-0 329 822 describes a primer construction for the generation of a double-stranded nucleic acid where the nucleic acid to be amplified is functionally linked to a promoter. In order to accomplish this, one of the primer contains at least one strand of a promoter region. The intermediately formed transcription complex is subject to conditions whereby, under control of the promoter, ribonucleic acids are formed while the nucleic acid to be amplified is used as a template. The so obtained ribonucleic acids are again used for the formation of a new transcribable nucleic acid complex. An advantage of this system is that it can be carried out as an isothermal process.

A multiplex PCR is understood to be a method according to EP-A-0 364 255. In this method, a single vessel reaction is used to amplify certain fragments of nucleic acids in a suitable arrangement of the hybridization position of numerous primers; said fragments usually differ in length and position of the genome.

The method of the invention is a special embodiment of so-called hybridization tests, the basics of which are known to the expert in the field of nucleic acid diagnostics. Unless experimental details are given in greater detail, reference is made to the complete contents of the "Nucleic acid hybridisation", B. D. Hames and S. J. Higgins, IRL Press, 1986, particularly Section 1 (Hybridisation Strategy), Section 3 (Quantitative Analysis of Solution Hybridisation) and Section 4 (Quantitative Filter Hybridisation), Current Protocols in Molecular Biology, Edt. F. M. Ausubel et al., J. Wiley and Son, 1987, particularly 2.9.1–2.9.10 and Molecular Cloning, Edt. J. Sambrook et al., CSH, 1989, particularly 9.4.7–9.5.8. This includes in particular known methods for the preparation of labelled nucleoside triphosphates as they are also described in EP-A-0 329 474, the chemical synthesis of modified and unmodified oligonuclectides, the cleavage of nucleic acids with the aid of restriction enzymes, the selection of hybridization conditions to achieve a given specificity which depends on the extent of the homology between the nucleic acids to be hybridized, their GC contents, and their length, and also the formation of nucleic acids from nucleoside triphosphates with the aid of polymerases.

A label as understood in the present invention is a directly or indirectly detectable group. Directly detectable groups are, for example, radioactive ($^{32}P$), dyed or fluorescent groups or metal atoms. Indirectly detectable groups include immunologically or enzymatically active compounds, such as antibodies, antigens, haptens, or enzymes, or enzymatically active partial enzymes. They are detected in a subsequent reaction or reaction sequence. Particularly preferred are haptens as the nucleoside triphosphates (rNTP or dNTP) which are labelled with such haptens), are generally particularly well used as substrates of (RNA and/or DNA) polymerases; subsequently, it is possible to carry out a reaction with a labelled antibody to the hapten or the haptenized nucleoside. Nucleoside triphosphates of this kind include bromonucleoside triphosphate or digoxigenin, digoxin, or fluorescein-coupled nucleoside triphosphates. The steroids described in EP-A-0 324 474 and their detection have proven to be particularly suitable. For their incorporation in nucleic acid, reference is made to EP-A-0 324 474.

Nucleic acids for use with the amplification and detection process for legionella in accordance with the invention are in particular genomic nucleic acids. Genomic nucleic acids contain also those genes that code for ribosomal RNA (rRNA) and a number of spacer sequences. They are given designations according to the size of the rRNA for which they code. In legionella genomes, this order of genes is as follows: 16S-rRNA-gene, the 23S-rRNA gene, and the 5S-rRNA gene. These genes are separated from one another by means of so-called spacer regions.

SEQ. ID. NO. 1 discloses a nucleotide sequence which bears similarity with a genomic sequence contained in the species of the genus legionella; said sequence includes two adjacent regions of the 23S-rRNA, the spacer region between 5S-rRNA and 23S-rRNA, and the 5S-rRNA. SEQ. ID. NO. 1 covers only a relatively small portion of the 23S-rRNA, however, it does include the complete spacer region and approx. 80% of the 5S-rRNA.

SEQ. ID. NO. 1 is a nucleotide sequence from which partial sequences that are genus-specific for legionella can be taken out.

As understood in the present invention, the term nucleic acid probe should not be considered limiting with respect to function. The aforementioned properties are critical. The nucleic acid probes should also cover so-called probes or detection probes whose hybridization with a legionella nucleic acid contained in the sample serves as a measure for the presence of the bacterium. To accomplish this, the nucleic acid probe can preferably contain parts which essentially do not negatively affect the detection or the amplification. Such molecule parts include, for example, labels for the detection of the probe, e.g. hybrids containing said probe, groups which allow immobilisation of the nucleic acid probe to a solid phase, solid phases as such (e.g. beads or surfaces, e.g. reagent or detection containers) or other nucleotide sequences which do not interfere with legionella sequences. The configuration of the nucleic acid probe, therefore, depends in particular upon the manner in which the legionella nucleic acids are to be detected.

A nucleic acid probe is understood to be a molecule with a defined order of bases and capable of forming natural nucleic acid hybrids based on base-to-base interaction. This includes natural and artificial nucleic acids. Artificial nucleic acids differ from natural nucleic acids in that they are modified either in the base portion (e.g. by using base analogs, e.g. 7-deaza-dGTP) or in the frame (substituting sugar and/or phosphate units by other chemical molecules, e.g. peptides). Such artificial nucleic acids are for example, the peptide nucleic acids (PNA) as described in WO 92/20702. An essential factor for correct functioning of nucleic acid probes is their specific base-pairing to achieve selectivity of the probes. It is particularly preferred to have a nucleic acid probe consisting of deoxyribonucleic acid (DNA).

A nucleic acid probe is also understood to be a primer which can be extended upon hybridization with lecionelia nucleic acids by using an enzyme. Typical extension reactions are, for example, the extension of mononucleoside triphosphate units by means of DNA polymerases (e.g. *E. coli* DNA-polymerase, Klenow fragment or Thermus aquaticus polymerase) using the legionella nucleic acid as a template. In this case, the 3'-end of the primer is extended with currently used enzymes. Another extension reaction is the ligase reaction, wherein the nucleic acid probe is enzymatically linked with another oligonucleotide (e.g. EP-A-0 320 308). Mixed forms consisting of polymerase and ligase reactions are also known (e.g. WO 90/01069).

A nucleic acid probe that is genus-specific for legionella is a nucleic acid which hybridizes with the nucleic acid having a nucleotide sequence according to SEQ. ID. NO. 1 or its complement, or one that hybridizes with all legionella species listed in Table 1 under identical stringent conditions. These nucleic acids preferably hybridize with all possible species of the genus legionella.

Genus-specific sequences of the sequence shown in FIG. 1 are preferably found in the 23S- and/or 5S region; provided that appropriate hybridization conditions are selected, it is also possible to design genus-specific probes in the spacer region.

TABLE 1

Expected length of amplificate in the 23S-5S spacer region when using the BID primer pair

| Species/Serogroup | ATCC No. (NCTC) | Strain | Amplicon length/ complete deter-mined length of sequence | EMBL Accession Number | SEQ ID. NO. |
|---|---|---|---|---|---|
| *L. pneumophila* sero 1 | 33152 | Philadelphia-1 | 232 bp/336 bp | Z30431 | 26 |
| *L. pneumophila* sero 1 | 33153 | Knoxville-1 | 232 bp/336 bp | Z30432 | 27 |
| *L. pneumophila* sero 1 | 43108 | Benidorm 030E | 232 bp/336 bp | Z30433 | 28 |
| *L. pneumophila* sero 1 | 43112 | France 5811 | 232 bp/336 bp | Z30534 | 29 |
| *L. pneumophila* sero 1 | 43109 | OLDA | 232 bp/336 bp | Z30434 | 30 |
| *L. pneumophila* sero 1 | 43110 | Oxford 4032E | 231 bp/335 bp | Z30435 | 31 |
| *L. pneumophila* sero 1 | 43113 | Camperdown-1 | 232 bp/336 bp | Z30436 | 32 |
| *L. pneumophila* sero 2 | 33154 | Togus-1 | 232 bp/336 bp | Z30437 | 33 |
| *L. pneumophila* sero 3 | 33155 | Bloomington-2 | 232 bp/336 bp | Z30438 | 34 |
| *L. pneumophila* sero 4 | 33156 | Los Angeles-1 | 232 bp/336 bp | Z30439 | 35 |
| *L. pneumophila* sero 4 | n.a. | Portland | 232 bp/336 bp | Z30440 | 36 |
| *L. pneumophila* sero 5 | 33216 | Dallas-1E | 232 bp/336 bp | Z30441 | 37 |
| *L. pneumophila* sero 5 | (11417) | Cambridge-2 | 232 bp/336 bp | Z30442 | 38 |
| *L. pneumophila* sero 6 | 33215 | Chicago-2 | 232 bp/336 bp | Z30443 | 39 |
| *L. pneumophila* sero 7 | 33823 | Chicago-8 | 232 bp/336 bp | Z30444 | 40 |
| *L. pneumophila* sero 8 | 35096 | Concord-3 | 232 bp/336 bp | Z30445 | 41 |
| *L. pneumophila* sero 9 | 35289 | IN-23-01-C2 | 232 bp/336 bp | Z30446 | 42 |
| *L. pneumophila* sero 10 | 43283 | Leiden-1 | 232 bp/336 bp | Z30447 | 43 |
| *L. pneumophila* sero 11 | 43130 | 797-PA-H | 232 bp/336 bp | Z30448 | 44 |
| *L. pneumophila* sero 12 | 43290 | 570-CO-H | 232 bp/336 bp | Z30449 | 45 |
| *L. pneumophila* sero 13 | 43736 | 82 A 31 05 | 232 bp/336 bp | Z30450 | 46 |
| *L. pneumophila* sero 14 | 43073 | 1169-MN-H | 232 bp/336 bp | Z30451 | 47 |
| *L. anisa* | 35292 | WA-316-C3 | 267 bp/371 bp | Z30535 | 48 |
| *L. brunensis* | n.a. | n.a. | 246 bp/350 bp | Z30536 | 49 |
| *L. cherrii* | 35252 | ORW | 258 bp/362 bp | Z30537 | 50 |
| *L. cincinnaliensis* | 43753 | 72-OH-H | 213 bp/317 bp | Z30452 | 51 |
| *L. dumoffii* | 33279 | NY-23 | 255 bp/359 bp | Z30538 | 52 |
| *L. erythra* | 35303 | SE-32A-C8 | 201 bp/325 bp | Z30453 | 53 |
| *L. feeleii* sero 1 | 35072 | WO-44C | 238 bp/342 bp | Z30454 | 54 |
| *L. feeleii* sero 2 | 35849 | 691-WI-H | 238 bp/342 bp | Z30455 | 55 |
| *L. israeiensis* | 43119 | Bercovier-4 | 217 bp/321 bp | Z30583 | 56 |
| *L. jordanis* | 33623 | BL-540 | 244 bp/348 bp | Z30539 | 57 |
| *L. longbeachae* sero 1 | 33462 | Long Beach-4 | 208 bp/312 bp | Z30456 | 58 |
| *L. longbeachae* sero 2 | 33484 | Tucker-1 | 208 bp/312 bp | Z30465 | 59 |
| *L. maceachernii* | 35300 | PX-1-02-E2 | 2S0 bp/352 bp | Z30461 | 60 |
| *L. micdadei* | 33218 | Tatlock | 267 bp/371 bp | Z30460 | 61 |
| *L. moravica* | n.a. | 316-36 | 236 bp/340 bp | Z30457 | 62 |
| *L. oakridgensis* | 33761 | OR-10 | 197 bp/302 bp | Z30540 | 63 |
| *L. rubriiucens* | 35304 | WA-270A-C2 | 219 bp/324 bp | Z30458 | 64 |
| *L. saintheiensi* | 35248 | Mt St Helens-4 | 212 bp/316 bp | Z30459 | 65 |
| *L. spiritensis* | 35249 | Mt St Helens-9 | 246 bp/350 bp | Z30464 | 66 |
| *L. steigerwaitii* | 35302 | SC-18-C9 | 256 bp/360 bp | Z30463 | 67 |
| *L. wadsworthii* | 33877 | 81-716A | 262 bp/366 bp | Z30462 | 68 |

Species-specific nucleic acid probe are nucleic acids which hybridize with all serovars of a legionella species under identical stringent conditions. Probes of this kind and their sequences are given in example 3. The example also includes an *L. pneumophila* species probe which hybridizes with all serovars of the species pneumophila, but not with all other species of the genus legionella as listed in Table 1.

The nucleic acid probe of the present invention has a minimum length of 15 bases, particularly preferred is a length of 23 to 40 bases. It is, hence, a nucleic acid which can be easily obtained by means of chemical synthesis on so-called (nucleic acid) synthesizers. Sequences which can be used as a genus-specific sequence for legionella can be obtained by selecting a sequence of SEG. ID. NO. 1 of at least 15 bases in length; a deviation of one or two bases in the genus specificity in dependency upon the hybridization conditions does normally not affect the procedure. It is understood that a number of deviations increases with an increasing size of the nucleic acid probe. The invention, therefore, prefers probes with at least 90% homology to a part of SEQ. ID. NO. 1 or which are at least 90% complementary to a part of SEG. ID. NO. 1. Particularly preferred are probes with a minimum sequence length of 15 bases (in direct order) that is strictly homologous or strictly complementary to a part of SEQ. ID. NO. 1.

The species specificity could be negatively affected if the probe contains additional legionella species specific sequences or non-legionella specific sequences which could lead to a specific and/or unspecific hybridization. Other legionella-specific sequences, if present at all, do not exceed 15 bases in length. Moreover, a nucleic acid probe may contain functional nucleotide sequences as they are characteristic for promoters or origins of replication and its legionella-unspecific region.

Within SEQ. ID. NO. 1, certain areas are particularly preferred for selecting genus-specific sequences, especially for detection probes. Particularly preferred regions are found between positions 94 and 126, 25 and 67, 336 and 293, and 307 and 286. In a particularly preferred manner, the sequence of the probe includes the sequence from position 268 to 296.

As opposed to prior art, the amplification method in accordance with the invention requires less than 7 primers.

This is accomplished in that one or several nucleic acid probes of the invention are used as primers. An amplification method which needs only one primer is obtained in that the primer hybridizes with the nucleic acid to be amplified; then it is extended with mononucleoside triphosphates under the aid of a DNA polymerase. The extension product is separated from the template nucleic acid and the above procedure is repeated with a new primer. Each cycle, hence, yields one extension product per nucleic acid. This is, hence, a linear amplification method. Exponential amplification is theoretically possible when two primers are used which satisfy the principle conditions as described in EP-A-0 201 184. An advantageous embodiment uses another primer pair which hybridizes on the nucleic acid fragment to be amplified between the hybridizing positions of the first primer pair. This embodiment is occasionally also referred to as “nested PCR”. It uses a total of 4 different primers.

Amplication methods that are based on transcription reactions usually employ two nucleic acid probes which can be hybridized either on counter-sense strands or on a strand of the nucleic acid to be amplified.

In accordance with the invention, the nucleic acid probes which act as primers in the genus-specific amplification method are legionella genus-specific probes. In a particularly preferred case, one of the primers hybridizes with the strand of the legionella nucleic acid in the 23S-rDNA region, while the other one hybridizes with the counter-strand in the 5S-rDNA region. The amplified part of the nucleic acid sequence of the legionella thus covers parts of the 23S-rDNA region as well as the 5S-rDNA region and also the spacer region therebetween. To facilitate understanding it is necessary to realize that the amplification products of different species differ in a sequence located between the ends facing each other of the original primer. This region preferably covers the sequences of the spacer region.

The genus-specific amplification method of the invention can be used to fulfill several purposes. In a first possibility (e.g. when used for screening) it is possible to detect the total of all species of the genus legionella present in a sample. This is possible when the amplificates obtained during genus-specific amplification are allowed to hybridize with another genus-specific nucleic acid probe (if necessary, detectably labelled), the so obtained hybrids can then be detected. The nucleic acid probe (detection probe) can be selected such that it hybridizes in the regions which are in the vicinity of the original primer hybridization sites; however, the specificity of the genus-specific detection is further increased when the nucleic acid probe hybridizes in the area of the amplificates that are located in the region of the primer ends which face one another. In a particularly preferred manner, the genus-specific detection probe hybridizes between positions 242 and 299 of SEQ. ID. NO. 1 and has a length between 25 and 35 nucleotides, preferably preferred 26 to 30 nucleotides. When the length of the probe is altered, the hybridization temperature must be modified accordingly. An optimal genus-specific probe hybridizes between positions 268 and 296 and has, hence, a length of 29 nucleotides.

Principally: it is possible to use all known detection formats for the detection of the amplificates, e.g. separation according to size (gel electrophoresis) but also blot methods. Based on the varying sizes of the spacer region, it is already possible to differentiate non-pneumophila species in a simple high-resolution agarose gel which proves rapid information for orientation which is usually done with screening methods. Usually, however, it is also necessary to carry out a detection which includes a hybridization step with a detection probe. The use of reverse dot blot format has proven to be particularly advantageous. To accomplish this, a genus-specific nucleic acid probe is immobilized on a membrane, while subsequently the product of the amplification reaction is added to the immobilized probes. This requires that the amplificates are available as single strands. If labelled mononucleoside triphosphates had been included during amplification, the detection via the amplificates that are immobilized via the nucleic acid probe can be easily done after washing off non-bound nucleic acids. Such a method is described in EP-A-0 237 362, for example. Reference is therefore made to the complete contents of said application.

Detection is, however: also possible with so-called sandwich assays, where an additional labelled genus-specific nucleic acid probe (detection probe) is used in addition to the mobilized nucleic acid probe. Said detection probe hybridizes with the amplificates at another position than the solid phase-bound probe. The principle of this assay is described in EP-B-0 079 139.

The genus-specific amplification method of the invention, however, also allows the reliable and simple detection of legionella species (e.g. the clinical routine) or mixtures of species (e.g. to differentiate *L. pneumphila* from non-pneumophila). In this case, the genus-specific amplification method can be followed by hybridization with a species-specific probe (if desired labelled) (detection probe) which hybridizes in the amplified region between two primer ends that are facing one another. SEQ. ID. NO. 26–68 shows sequences from which the species-specific sequences can be selected for an individual species. The species-specific parts are located particularly in the spacer region which is preferably amplified with the aid of a genus-specific primer. The location of the amplificates (e.g. as indicated in Table 1) can be obtained from the hybridization positions of the primers (in Table 1. this is primer pair B/D). Particularly preferred species-specific detection probes are given in example 3.7. Species-specific detection probes which are based on these spacer sequences are preferably longer than 15 bp and shorter than the entire spacer region.

The method of the invention, hence., allows the multiple detection of legionella species using one single reaction mixture obtained in a preceding genus-specific amplification reaction; said reaction mixture contains the amplificates of parts of the legionella species present in the probe It is, hence, an advantage of the invention that it allows a more simple, e.g. less complex detection of bacteria of the genus legionella.

Another subject matter of the invention is, hence, a pair of primers for amplifying legionella-nucleic acid where one hybridizes with the strand of the 23S region while the other hybridizes with the counter-strand in the 5S region of the legionella genome.

Another subject of the invention is a double-stranded legionella-specific nucleic acid containing the spacer region between 5S-rDNA and 23S-rDNA and only those regions of the 5S-rDNA and 23S-DNA which directly follow the spacer region in the genome. In a preferred manner, this is a double-stranded nucleic acid of a maximum length of 371 bp and is the product of a genus-specific amplification reaction.

Yet another subject matter of the invention is reagent kit for the detection of legionella species comprising at least one legionella genus-specific nucleic acid and at least one legionella-species-specific probe.

The following examples explain the invention in greater detail:

EXAMPLE 1

Obtaining and Growing Bacteria

The legionella "type strains" used here were grown on buffered yeast-charcoal extract agar (P. H. Edelstein, Laboratory Diagnosis of infections caused by legionellae, Eur. J. Clin. Microbiol. Vol. 6, 1, 4–10 (1987)) with the addition of α-ketoglutarate at an incubation temperature of 35° C. and a humid $CO_2$ atmosphere for at least 3 days. Gramstaining, microscopy and incubation of blood agar plates did not reveal the growth of any other bacteria. The legionella were harvested from the plates with 3 ml redistilled water, diluted, and centrifuged at 12,000 g. The supernatant was discarded, and the cell pellet resuspended in 500 μl of re-distilled water. Logarithmic serial dilution and counting of the colonies on agar plates yielded an average of $10^{10}$ KBE/ml.

EXAMPLE 2

DNA Digestion

Aliquots of 250 μl of the respective bacteria culture were lysed in alkaline environment to release the DNA (PCR: Clinical diagnostics and research; Springer Verlag Berlin/Heidelberg 1992, p. 79–80) by adding 250 μl of 250 mM NaOH solution; Then, they were covered with 100 μl mineral oil (Sigma) and incubated for 20 min in a thermal mixer that was heated up to 95° C. After agitation and centrifugation, 32 μl of Tris-HCI (pH 5.0) were added for neutralization, then the mixture was again agitated and centrifuged. Control samples with redistilled water were treated identically to identify possible contamination during the sample preparation.

The so obtained nucleic acid could now be used in amplification and hybridization experiments.

EXAMPLE 3

Detection of Legionella (Genus and Species)

Legionella were detected by employing genus-specific amplification in accordance with the invention while incorporated digoxigenin labelled dUTP. The labeled amplificates were then detected via reverse dot blot technique (Kawasaki et al., Genetic analysis using polymerase chain reaction—amplified DNA and immobilized oligonucleotide probes: reverse dot-blot typing; in: Methods in Enzymology, Vol. 218, 1993).

1. Probe Preparation (Tailing Reaction)

Boehringer Mannheim Terminal Transferase Kit 220–582

200 pmol oligonucleotide

20 μl 5×reaction buffer

6 μl 25 mM $CoCl_2$ (final concentration: 1.5 mM)

8 μl 10 mM dTTP (total amount: 80 nmol)

2.4 μl terminal transferase (60 U)

dd$H_2O$ to 100 μl.

The mixture was incubated for 1 hour at 37° C.

2. Polymerase Chain Reaction (PCR) and Digoxigenin Labelling of the PCR Products PCR 25 μl mixtures:

3.75 μl dNTPs (1 mM conc.)

1.25 Boehringer DIG DNA labeling mixture 2.5 μl Perkin-Elmer Buffer 1

0.75 μl primer each (stock solution 10 μM)

1 μl Taq Polymerase (Perkin-Elmer) (diluted 1:10)

$H_2O$ to 24 μl

1 μl DNS

Thermoprofile (Primer B & D; Perkin-Elmer 9600 Thermocycler)

95°–3 min

95°–30 sec; 54°–25 sec; 72°–30 sec: 30 cycles

72°–5 min cool down to 6° C.

3. Preparation of the Membranes

Boehringer Mannheim positively charged Nylon membranes were cut into thin strips. They were marked with pencil and a 1 ml pipette with the tip cut-off was used to punch circles into the membrane. 1 μl (2 pmol) of probe were added, allowed to dry for 10 min at air and cross-linked with 120 ml Stratalinker® (Stratagene).

The membrane was washed (to remove non-bound probe): (all strips together in one 50 ml Falcon® tube)

Washing solution: 5×SSPE, 0.5% SDS 30 min at 61°

Washed with redistilled water

Allowed to dry at air, strips can then be stored after this step at −20° C.

4. Hybridization

Prehybridization—in individual numbered Eppis (Eppendorf vessels)

| | |
|---|---|
| Solution (portions of 300 ml) | 5 x SSPE<br>0.5% SDS<br>0.5% dextrane sulfate |

30 min at 61°.

Hybridization

PCR product is denatured for 10 min at 95° and then rapidly added after the end of the prehybridization phase.

While softly rotating, it is allowed to hybridize for exactly 1 hour at 61°

After Completion of the Hybridization, the Membranes are Washed (in the same Eppendorf Vessel with Portions of 300 μl of the following Solution

2×SSPE 0.1% SDS

Washing steps (while slightly agitated): twice 5 min at room temperature and once 10 min at 65° C.

5. Detection

All steps were carried out under slight shaking in a 50 ml Falcon tube (buffer volume approx. 30 ml) (Boehringer Mannheim Cat. No. 117504).

a) 30 min D1 buffer b) 30 min D2 buffer c) Mix 3 μl antibody conjugate solution with 30 ml fresh D2 buffer and incubate for 30 min d) 2×15 min D1 buffer e) Short incubation in D3 buffer f) The membranes are placed in a transparent cover with the DNA side up:
45 μl NBT
35 μl X phosphate solution
10 μl D3 buffer g) The color solution is added: the membrane must not move. Allow to develop for exactly 15 min.

h) Stopping solution: D4 buffer i) Allow to dry at air

Buffer

| 20 x SSPE | 3M NaCl 175,3 g NaCl |
| --- | --- |
| | 0,2 M Na$_2$H$_2$PO$_4$   27,6 g Na$_2$H$_2$PO$_4$ |
| | 20 mM EDTA    7,4 g EDTA |
| | pH 7,4 adjust with NaOH, redist. water. |
| | ad 1.000 ml |
| 2 x SDS | 20 g SDS |
| | pH 7,2 adjust with HCl (a few drops), |
| | redist. water ad 1.000 ml |
| D1 | 100 mM maleic acid |
| | 150 mM NaCl |
| | 0,3% (w/v) Tween 20 |
| | pH 7,5 20° adjust with NaOH |
| D2 | 1,0% Blocking reagent (Kasein, Boehringer Kit), |
| | dissolved in |
| | D1, prepare 1 hour prior to use; store at −20°. |
| D3 | 100 mM Tris HCl |
| | 100 mM NaCl |
| | 50 mM MgCl2 |
| | adjust to pH 9,5 at 20° |
| D4 | 10 mM Tris HCl |
| | 1 mM EDTA |
| | adjust to pH 8,0 |

6. PCR-Primer

```
18mer:   5'-GGCTGATTGTCTTGACCA-3'     (Primer B)  SEQ.ID.No. 2
20mer:   5'-AGGAAGCCTCACACTATCAT-3'   (Primer D)  SEQ.ID.No. 3
24mer:   GTTGAAGACTACGACGTTGATAGG     (Primer A)  SEQ.ID.No. 4
21 mer:  AATGTTTCACTTCTGAGTTCG        (Primer C)  SEQ.ID.No. 5
```

7. Oligonucleotide probes (5S-rDNA)

Genus probe:
29mer:
5'-AACCACCTGATACCATCTCGAACTCAGAA-3' SEQ. ID.No.6

*L. pneumophila*-species probe:
31mer:
5'-ACGTGAAACGTATCGTGTAAACTCTGACTC-3' SEQ. ID.No. 7

*L. anisa*-species probe:
36mer: 5'-ATGCGAATACAAGATGTAGGTTGGGC-3' SEQ. ID. No. 8

*L. micdadei*-species probe:
34mer:
5'-ATGTAAATTGCTCAGACAAATGAATACAGA-GTTT-3' SEQ.ID.No. 9

*L. brunensis*-species probe:
31mer:
5'-CCTGTTTTTACAGAGCACTTAACAATGCTCT-3' SEQ.ID.No. 10

*L. cherrii*-species probe:
29mer:
5'-AATGCAAATACAAGAAATTTAGGTTGGGC-3' SEQ. ID. No. 11

*L. cincinnattiensis*-species probe:
27mer: 5'-CTCTCTTTRTTTACCGGAAGTAACGCG-3' SEQ.ID.No. 12

*L. dumoffii*-species probe:
26mer: 5'-ATCAATACCTGGGGTAGGACACCTGC-3' SEQ. ID. No. 13

*L. erythra*-species probe:
24mer: 5'-AACCCGGGTAAGACCGGAAAAACC-3' SEQ.ID.No. 14

*L. feeleii*-species probe:
27mer: 5'-GCAAAAATGAAAGACAAATGCGTTTGT-3' SEQ. ID.No. 15

*L. israelensis*-species probe:
27mer: 5'-TTAAACGCTTGTGAATCAAACCCATTC-3' SEQ. ID. No. 16

*L. jordanis*-species probe:
27mer: 5'-TGATGAATGAATATCCCCTAACATGGG-3' SEQ.ID.No. 17

*L. longbeachae*-species probe:
39mer: 5'-TGCTTGATATAAGATATAATACCTC-TTTATTTAC CTGAG-3' SEQ. ID. No. 18

*L. maceachernii*-species probe:
32mer: 5'-GGCAATACTTTAATTAAAGGCATTAATG-CCTA-3' SEQ. ID. No. 19

*L. moravica*-species probe:
23mer: 5'-AGGCCTTGGGCTTGTTGATTGAA-3' SEQ.ID.No. 20

*L. sainthelensi*-species probe:
40mer:
5'-GTGCTGAATATAAGATATAATGTTACTCTC-TTTATTTACC-3' SEQ. ID. No. 21

*L. spiritensis*-species probe:
25mer: 5'-GTGTGCCCTGAAGAAGAAACAGGGT-3' SEQ. ID. No. 22

*L. steigerwaltii*-species probe:
28mer:
5'-AATGTGTATACAAGCTGTAGGTTGGCCA-3' SEQ. ID. No. 23

*L. wadsworthii*-species probe:
30mer-
5'-GTACGTACGAATTAGAGATTGGGTCTAGGC-3' SEQ. ID. No. 24

8. Detection Methods a) Reverse dot blot hybridization with 4 different probes

According to the above working protocol, a detection method using the genus-specific amplification method and a genus (A) and/or 3-species-specific (B: *L. pneumophila*; C: *L. anisa*: D: *L. micdadei*) probes was carried out. FIG. 2 shows the color development on 10 filters. It can be clearly seen that the genus specific probe (A) generates in every case a detection signal. The *L. pneumophilia*-specific probe (D) reacts only with a filter which also contains serovar 1, Philadelphia of *L. pneumophila*. The *L. anisa*-specific probe (C) generates a clear signal in filter No. 4. Species of *L. micdadei* can only be detected with the *L. micdadei*-specific probe (D). *L. gormanii* can only be detected with the genus-specific probe (filter No. 9).

The following nucleic acids were placed on the following filters:

1: *L. dumofii* (2pmol probe)
2: *L. anisa* (2pmol probe)
3: *L. anisa* (4pmol probe)
4: *L. anisa* (8pmol probe)
5: *L. micdadei* ATCC 33218 (2 pmol probe)
6: *L. micdadei* ATCC 33218 (4 pmol probe)

7: *L. micdadei* L 5443/90 (2 pmol probe)

8: *L. micdadei* L 5443/90 (4 pmol probe)

9: *L. gormanii*

10: *L. pneumophila* sero 1 Philadelphia

Figure 3:
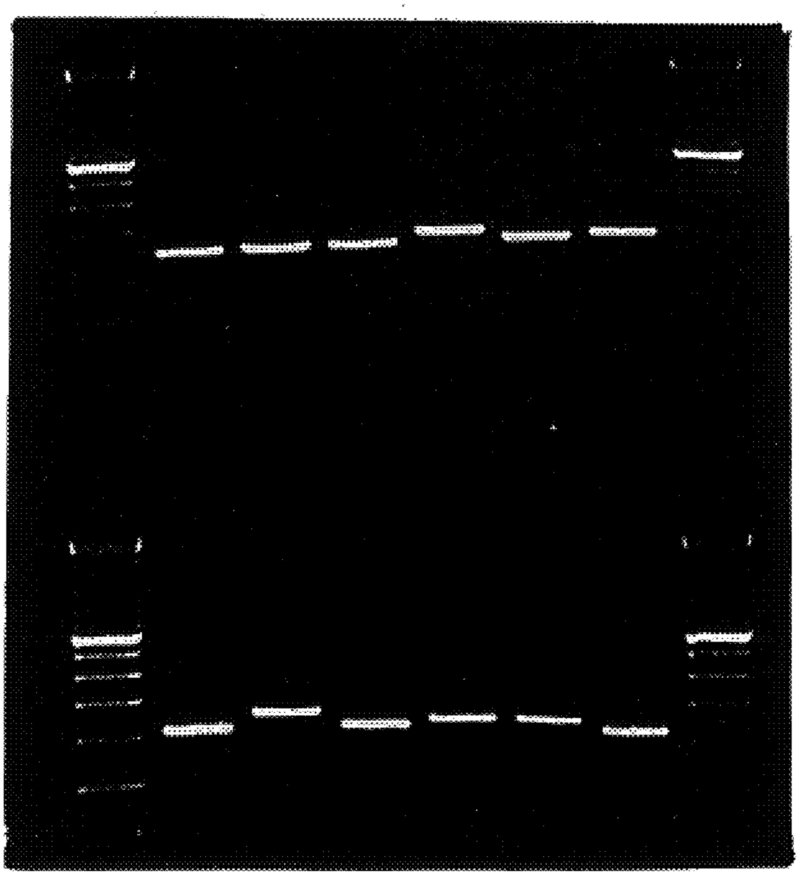
FIGS. 3, 4 and 5 show the results of the amplification of the 23S-5S-spacer region using the genus specific primers of the invention.
Figure 4:
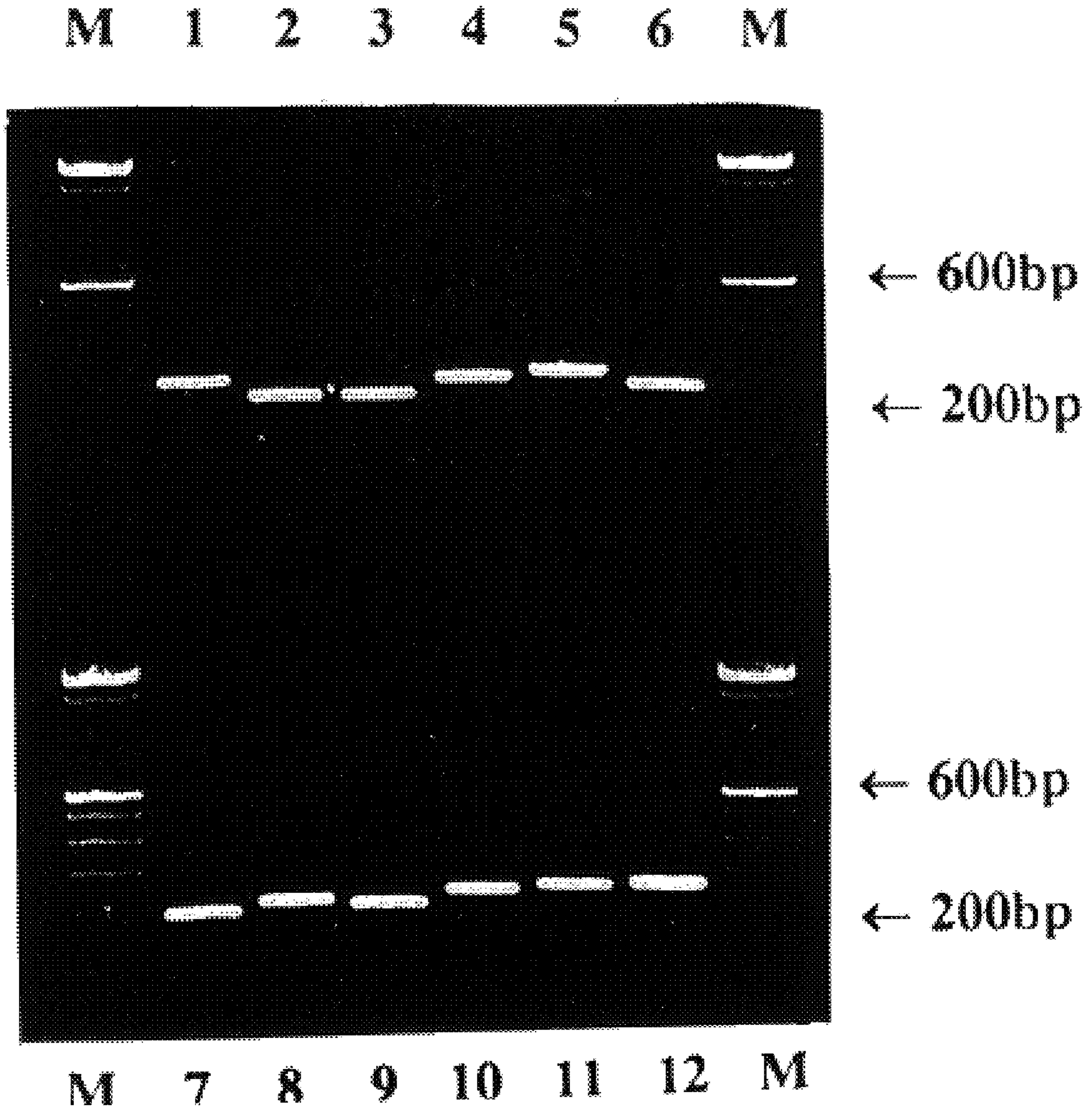
Figure 5:
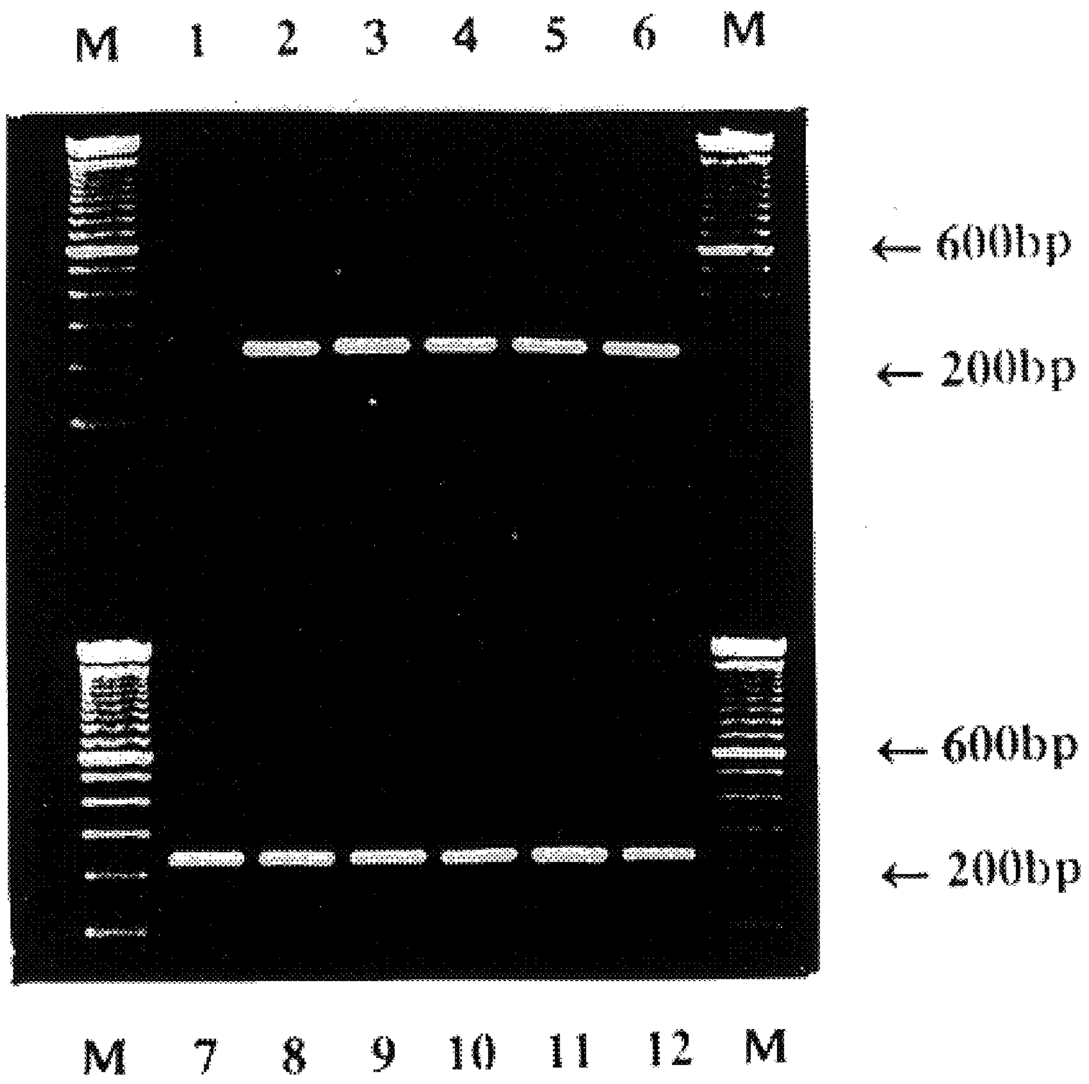

Amplification of the 23S-5S-spacer region of pneumophila and non-pneumophila species FIGS. 3, 4, and 5 show the result of the amplification of the 23S-5S-spacer region using the genus-specific primer of the present invention. It can be clearly seen that an amplification occurs in any case while in many cases there is a difference in the size of the amplificates of the individual species. It is hence possible to differ legionella species according to genus-specific amplification based on the size of the amplificates.

1: *L. pneumophila* sero 12 570-CO-H (FIG. 3)

2: *L. pneumophila* sero 13

3: *L. pneumophila* sero 14 1169-MN-H

4: *L. anisa* WA-316-C3

5: *L. brunensis*

6: *L. cherii* ORW

7: *L. cincinattensis* 72-OH-H

8: *L. dumofii* NY-23

9: *L. erythra* SE-32A-C8

10: *L. feeleii* sero 1 WO-44C

11: *L. feeleii* sero 2 691-Wl-H

12: *L. israelensis* Bercovier-4

M: 100 bp DNA size marker

1: *L. jordanis* B-L-540

2: *L. longeachae* sero 1 Long Beach-4

3: *L. longbeachae* sero 2 Tucker-1

4: *L. maceachernii* PX-1-G2-E2

5: *L. micdadei* TATLOCK

6: *L. moravica* 316–36

7: *L. oakridgensis* OR-10

8: *L. rubrilucens* WA-270-C2

9: *L. sainthelensi* Mt. St. Helens-4

10: *L. spiritensis* Mt. St. Helens-9

11: *L. steigerwaltil* SC-18-C9

12: *L. wadsworthii* 81-716A

M: 100 bp DNA size marker 1 negative control

2: *L. pneumophila* sero 1 Philadelphia 1

3: *L. pneumophila* sero 2 Togu-1

4: *L. pneumophila* sero 3 Bloomington-2

5: *L. pneumophila* sero 4 Los Angeles-1

6: *L. pneumophila* sero 5 Dallas-1E

7: *L. pneumophila* sero 6 Chicago-2

8: *L. pneumophila* sero 7 Chicago-8

9: *L. pneumophila* sero 8 Concord-3

10: *L. pneumophila* sero 9 IN-23-G1-C2

11: *L. pneumophila* sero 19 Leiden-1

12: *L. pneumophila* sero 11 797-PA-H

M: 100 bp DNA size marker

Instead of the primers B and D used in example 3, it is also possible to use primers with different hybridization positions on SEQ. ID. NO. 1. The following are concrete hybridization positions (first base-pairing and length) of additional primers. Suitable probes are also given with respect to the genus-specific probe. The list also shows particularly suitable combinations of primers for a genospecific amplification

EXAMPLE 4

Possible Variations for Primers and Probes

Primer

Primer B—possible variants

1) Pos. 104, 18 mer, $T_m$ 43,9° (Primer B from example 3)

2) Pos. 105, 21 mer, $T_m$ 43,0°

3) Pos. 110, 22 mer, $T_m$ 42,8°

4) Pos. 103, 18 mer, $T_m$ 43,9°

5) Pos. 101, 19 mer, $T_m$ 42,7°

6) Pos. 100, 19 mer, $T_m$ 43,5°

7) Pos. 99, 20 mer, $T_m$ 44,2°

8) Pos. 100, 20 mer, $T_m$ 45,0°

9) Pos. 98, 20 mer, $T_m$ 43,5°

10) Pos. 94, 21 mer, $T_m$ 43,1°

11). Pos. 104, 19 mer, $T_m$ 45,2°

12) Pos. 105, 23 mer, $T_m$ 46,1°

13) Pos. 113, 23 mer, $T_m$ 44,7°

14) Pos. 102, 19 mer, $T_m$ 46,3°

15) Pos. 100, 20 mer, $T_m$ 45,0°

16) Pos. 99, 21 mer, $T_m$ 45,6°

17) Pos. 98, 21 mer, $T_m$ 45,8°

18) Pos. 96, 22 mer, $T_m$ 45,5°

19) Pos. 105, 22 mer, $T_m$ 45,1°

20) Pos. 109, 23 mer, $T_m$ 44,0°

Primer D—possible variants

21) Pos. 316, 20 mer, $T_m$ 43,7° (Primer D from example 3)

22) Pos. 312, 19 mer, $T_m$ 46,0°

23) Pos. 317, 20 mer, $T_m$ 44,9°

Primer A:

1) Pos. 34, 21 mer, $T_m$ 44,5°

2) Pos. 35, 22 mer, $T_m$ 45,4°

3) Pos. 37, 21 mer, $T_m$ 44,5°

4) Pos. 39, 20 mer, $T_m$ 44,6°

5) Pos. 38, 29 mer, $T_m$ 42,1°

6) Pos. 31, 18 mer, $T_m$ 43,1°

7) Pos. 29, 18 mer, $T_m$ 45,9°

8) Pos. 27, 18 mer, $T_m$ 43,2°

9) Pos. 25, 18 mer, $T_m$ 45,4°

10) Pos. 41, 19 mer, $T_m$ 43,8°

Primer C:

11) Pos. 286, 21 mer, $T_m$ 44,7°

12) Pos. 286, 20 mer, $T_m$ 42,4° possible variants of the 5S-genus probe (for primer combination B/D only)

Pos. 268, 29 mer. $T_m$ 61,0° (probe used in example 3)

Pos. 269, 29 mer: $T_m$ 60,7°

Pos. 270, 29 mer, $T_m$ 60,7°

Pos. 271, 30 mer, $T_m$ 61,5°

Pos. 267, 29 mer, $T_m$ 61,4°

Pos. 265, 27 mer, $T_m$ 60,6°

23S Genus probe (suitable for primer combination A/C)

5'-TTGTAGTAATTGGCTGATTGTCTTGACCATA-3'SEQ.ID.No. 25

Possible variants of the L-pheumophila species (suitable for primer combinations B/D and A/C)

Pos. 162, 39 mer, $T_m$ 59,1° (probe used in example 3)

Pos. 160, 32 mer, $T_m$ 59,3°

Pos. 163, 31 mer, $T_m$ 60,1°

Pos. 159, 33 mer, $T_m$ 59,4"

The positions (5'-terminal base) are referred to the sequence given in FIG. 1 with primer A and B being complementary to parts of the sequence given in FIG. 1; they begin at the respective positions, and primers D and C are sequence-identical to parts of the sequence of FIG. 1) beginning at the respective positions and continued downstream (beginning from the sequence given in FIG. 1).

Primer combinations

| Primer B/D | Primer A/C |
|---|---|
| 1/21 | 1/11 |
| 2/21 | 2/11 |
| 3/21 | 3/11 |
| 5/21 | 4/11 |
| 6/21 | 5/12 |
| 7/21 | 6/12 |
| 9/21 | 7/11 |
| 10/21 | 8/12 |
| 11/22 | 9/11 |
| 12/22 | 10/11 |
| 13/22 | |
| 14/22 | |
| 15/22 | |
| 16/22 | |
| 17/22 | |
| 18/22 | |
| 11/23 | |
| 4/23 | |
| 19/23 | |
| 20/23 | |
| 8/23 | |
| 17/23 | |

All primers and nucleotide sequences are DNAs (oligonucleotides in the case of primers and probes) linear single-stranded.

The probes of the invention are preferably specific for legionella, i.e. they do not exhibit any interaction as primer and/or detection probes for organisms which do not belong to the genus legionella. The primer pairs B/D and A/C were not characterized as being effective with respect to *Bacillus cereus, Branhamella catharrhalis, Candida albicans, Chlamydia trachomatis, Corynebacterium diphtheriae*, Cryptococcus, *Escherichia coli, Haemophilus influenzae*, Lactobacterium, *Listeria monocytogenes, Mycobacterium africanum*, avium, bovis, flavescens, fortuitum, gordanae, kansasii, terrae and xenopisis, *Neisseria meningitidis*, Nocardia, *Proteus vulgaris, Pseudomonas aeruginosa*, Rhodococcus, *Salmonella enteriditis, Staphylococcus aureus, Streptocccous faecalis*, milleri, pneumoniae and viridans and β-hemolytic *Streptococcus pyogenes, Trichomonas vaginalis* and *Vibrio cholerae*.

We claim:

1. A method of amplifying a nucleic acid of the genus legionella, comprising:

(a) hybridizing two nucleic acid primers that are genus-specific for legionella with the legionella nucleic acid, to form a hybrid, wherein each of the two nucleic acid primers independently comprises a sequence of at least 15 bases, which sequence is, in direct order, at least 90% identical to a portion of SEQ ID NO: 1, or a complement thereof, which portion contains a same number of bases as the sequence;

(b) extending the nucleic acid primers of the hybrid to form extension products using the legionella nucleic acid as a template;

(c) separating the extension products and the legionella nucleic acid; and (d) repeating steps (a)–(c) at least once to amplify the nucleic acid of the genus legionella.

2. The method of claim 1, wherein the legionella nucleic acid is a genomic nucleic acid.

3. The method of claim 1, wherein the nucleic acid primers are extended using a polymerase chain reaction.

4. The method of claim 1, wherein the nucleic acid primers are extended using a ligase reaction.

5. The method of claim 1, wherein the nucleic acid primers hybridize, under stringent conditions, with all species of the genus legionella, while hybridization with non-legionella species is avoided.

6. The method of claim 1, wherein each of the two nucleic acid primers independently comprises a sequence of at least 15 bases which sequence is, in direct order, identical to portion of SEQ ID NO: 1, or a complement thereof, which portion contains a same number of bases as the sequence.

7. The method of claim 1, wherein one of the two nucleic acid primers comprises a sequence of at least 15 bases, which sequence is, in direct order, identical to (a) a portion of positions 94–126 of SEQ. ID. NO. 1, or a complement thereof, which portion contains a same number of bases as the sequence; or (b) a portion of positions 25–67 of SEQ. ID. NO. 1, or a complement thereof, which portion contains a same number of bases as the sequence.

8. The method of claim 1, wherein the sequence is 23 to 40 bases.

9. The method of claim 1, wherein in step (a), one nucleic acid primer hybridizes with a first strand of the legionella nucleic acid in the 23S-rDNA region of the legionella nucleic acid, while the other nucleic acid primer hybridizes with the counterstrand of the legionella nucleic acid in the 5S-rDNA region of the legionella nucleic acid.

10. The method of claim 1, wherein the two nucleic acid primers comprise deoxyribonucleic acid.

11. A method of detecting a nucleic acid of the genus legionella, comprising:

(a) hybridizing two nucleic acid primers that are genus-specific for legionella with the legionella nucleic acid, to form a hybrid, wherein each of the two nucleic acid primers independently comprises a sequence of at least 15 bases, which sequence is, in direct order, at least 90% identical to a portion of SEQ ID NO: 1, or a complement thereof, which portion contains a same number of bases as the sequence;

(b) extending, in an extension region, the nucleic acid primers of the hybrid to form extension products using the legionella nucleic acid as a template;

(c) separating the extension products and the legionella nucleic acid;

(d) repeating steps (a)–(c) at least once;

(e) thereafter hybridizing the extension products with a detection probe; and (f) detecting the hybrid formed in step (e) to thereby detect the nucleic acid of the genus legionella.

12. The method of claim 11, wherein one nucleic acid primer hybridizes with a first strand of the legionella nucleic acid at a first hybridization site, while the other nucleic acid primer hybridizes with the counterstrand of the legionella nucleic acid at a second hybridization site, wherein the one nucleic acid primer has a first primer end which faces upstream from the first hybridization site and the other nucleic acid primer has a second primer end which faces downstream from the second hybridization site, and the first primer end and the second primer end face one another, thereby defining the extension region of each nucleic acid primer, located between the first primer end and the second primer end.

13. The method of claim 12, wherein the detection probe hybridizes with one of the extension products in the extension region.

14. The method of claim 11, wherein each of the two nucleic acid primers independently comprises a sequence of at least 15 bases, which sequence is, in direct order, identical to a portion of SEQ ID NO: 1 or a complement thereof, which portion contains a same number of bases as the sequence.

15. The method of claim 11, wherein the sequence is 23 to 40 bases.

16. The method of claim 11, wherein the sequence is, in direct order, identical to a portion selected from the group consisting of (a) a portion of positions 94–126 of SEQ. ID. NO. 1, or a complement thereof, which portion contains a same number of bases as the sequence;

(b) a portion of positions 25–67 of SEQ. ID. NO. 1, or a complement thereof, which portion contains a same number of bases as the sequence;

(c) a portion of positions 336–293 of SEQ. ID. NO. 1, or a complement thereof, which portion contains a same number of bases as the sequence; and (d) a portion of positions 307–286 of SEQ. ID. NO. 1, or a complement thereof, which portion contains a same number of bases as the sequence.

17. The method of claim 11, wherein the extension products comprise a nucleic acid region which is identical to positions 242–299 of SEQ. ID. NO. 1, wherein the detection probe hybridizes with the extension products in the region, and wherein the detection probe is 25 to 35 bases in length.

18. The method of claim 17, wherein the detection probe is 26 to 30 bases in length.

19. The method of claim 11, wherein one of the extension products comprises a nucleic acid region which is identical to positions 268–296 of SEQ. ID. NO. 1, and wherein the detection probe hybridizes with the extension product in the region.

20. The method of claim 11, wherein the detecting step (f) comprises reverse dot blot detection.

21. The method of claim 11, wherein the detecting step (f) comprises a sandwich assay.

22. The method of claim 11, wherein the detection probe is species-specific for a species of the genus legionella.

23. A method of detecting a nucleic acid of a species of the genus legionella, comprising:

(a) hybridizing two nucleic acid primers that are genus-specific for legionella with the species nucleic acid, to form hybrids, wherein each of the two nucleic acid primers independently comprises a sequence of at least 15 bases, which sequence is, in direct order, at least 90% identical to a portion of SEQ ID NO: 1, or a complement thereof, which portion contains a same number of bases as the sequence, wherein one nucleic acid primer hybridizes with a first strand of the species nucleic acid at a first hybridization site, while the other nucleic acid primer hybridizes with the counterstrand of the species nucleic acid at a second hybridization site, wherein the one nucleic acid primer has a first primer end which faces upstream from the first hybridization site and the other nucleic acid primer has a second primer end which faces downstream from the second hybridization site, and the first primer end and the second primer end face one another, thereby defining an extension region of each nucleic acid primer, located between the first primer end and the second primer end;

(b) extending, in the extension region, the two nucleic acid primers of the hybrid to form extension products, using the species nucleic acid as a template;

(c) separating the extension products and the species nucleic acid;

(d) repeating steps (a)–(c) at least once;

(e) thereafter hybridizing at least one extension product with a detection probe which is species-specific for the nucleic acid of the species of the genus legionella to be detected; and (f) detecting the hybrid formed in step (e) to thereby detect the nucleic acid of the species of the genus legionella.

24. The method of claim 23, wherein the detection probe hybridizes with the at least one extension product in the extension region.

25. The method of claim 23, wherein the detection probe comprises a detection sequence of more than 15 bases, which detection sequence is, in direct order, identical to a portion of a sequence selected from the group consisting of SEQ. ID. NO. 26–SEQ. ID. NO. 68, which portion contains a same number of bases as the detection sequence.

26. The method of claim 23, wherein the detection probe comprises a detection sequence of more than 15 bases, which detection sequence is, in direct order, identical to a portion of the spacer region located between the 23S-rDNA region and the 5S-rDNA region of a sequence selected from the group consisting of SEQ. ID. NO. 1 and SEQ. ID. NO. 26–SEQ. ID. NO. 68, which portion contains a same number of bases as the detection sequence.

27. The method of claim 23, wherein the detection probe comprises a detection sequence of more than 15 bases, which detection sequence is, in direct order, identical to a portion of a sequence selected from the group consisting of SEQ. ID. NO. 7–SEQ. ID. NO. 24, which portion contains a same number of bases as the detection sequence.

28. The method of claim 23, wherein each of the two nucleic acid primers independently comprises a sequence of at least 15 bases, which sequence is, in direct order, identical to a portion of SEQ ID NO: 1, or a complement thereof, which portion contains a same number of bases as the sequence.

29. The method of claim 23, wherein one of the two nucleic acid primers comprises a sequence of at least 15 bases, which sequence is, in direct order, identical to (a) a portion of positions 94–126 of SEQ. ID. NO. 1, or a complement thereof, which portion contains a same number of bases as the sequence; or (b) a portion of positions 25–67 of SEQ. ID. NO. 1, or a complement thereof, which portion contains a same number of bases as the sequence.

30. The method of claim 23, wherein the sequence is 23 to 40 bases.

31. The method of claim 23, wherein the first hybridization site is within the 23S-rDNA region of the species nucleic acid, and the second hybridization site is within the 5S-rDNA region of the species nucleic acid.

32. A method of detecting a nucleic acid of the genus legionella and at least one species of the genus legionella in a single amplification reaction mixture, the method comprising:

(a) in an amplification reaction mixture, hybridizing two nucleic acid primers that are genus-specific for legionella with the legionella nucleic acid, to form a hybrid, wherein each of the two nucleic acid primers independently comprises a sequence of at least 15 bases, which sequence is, in direct order, at least 90% identical to a portion of SEQ ID NO: 1, or a complement thereof, which portion contains a same number of bases as the sequence, wherein one nucleic acid primer hybridizes with a first strand of the legionella nucleic acid in the 23S-rDNA region of the legionella nucleic acid, while the other nucleic acid primer hybridizes with the counterstrand of the legionella nucleic acid in the 5S-rDNA region of the legionella nucleic acid;

(b) extending, in an extension region, the nucleic acid primers of the hybrid to form extension products using the legionella nucleic acid as a template;

(c) separating the extension products and the legionella nucleic acid;

(d) repeating steps (a)–(c) at least once to produce amplification products comprising sequences in the 23S-rDNA region, the 23S-5S spacer region and the 5S-rDNA region of the legionella nucleic acid;

thereafter, in the same amplification reaction mixture, (e) hybridizing the amplification products with a detection probe which hybridizes with the amplification products in the 23S-rDNA region or the 5S-rDNA region;

(f) detecting the hybrid formed in step (e) to thereby detect the nucleic acid of the genus legionella;

(g) hybridizing the amplification products with a detection probe which hybridizes with the amplification products in the 23S-5S spacer region; and (h) detecting the hybrid formed in step (g) to thereby detect the nucleic acid of the species of the genus legionella.

33. The method of claim 32, further comprising detecting a plurality of legionella species in the same amplification reaction mixture by repeating steps (g) and (h) for each of the plurality of legionella species, using a different species-specific detection probe for each of the plurality of legionella species.

* * * * *

SEQUENCE LISTING (1) GENERAL INFORMATION:

(iii) NUMBER OF SEQUENCES: 68

(2) INFORMATION FOR SEQ ID NO: 1:

(i) SEQUENCE CHARACTERISTICS:
(A) LENGTH: 336 base pairs
(B) TYPE: nucleic acid
(C) STRANDEDNESS: single
(D) TOPOLOGY: linear (ii) MOLECULE TYPE: nucleic acid (xi) SEQUENCE DESCRIPTION: SEQ ID NO: 1:

```
GCCTCCCTCA AGATGAGTTT TCCCATGAAG CCCGTTGAAG ACTACGACGT TGATAGGCAA     60

GGTGTGGAAG CGCAGTAATG CGTGAAGCTA ACTTGTACTA ATTGGCTGAT TGTCTTGACC    120

ATATAATCTG AGTGACTTCA GAATGTGATA TTGATTTGTA TACGTGAAAC GTATCGTGTA    180

AACTCTGACT CTTTACCAAA CCTGTGGCTT AATATAGCAA TCAAAGCCTC AGGTAAACCA    240

GTTTTCCTGG CGACTATAGC GATTTGGAAC CACCTGATAC CATCTCGAAC TCAGAAGTGA    300

AACATTTCCG CGCCAATGAT AGTGTGAGGC TTCCTC                              336
```

(2) INFORMATION FOR SEQ ID NO: 2:

(i) SEQUENCE CHARACTERISTICS:
(A) LENGTH: 18 base pairs
(B) TYPE: nucleic acid

-continued (C) STRANDEDNESS: single
(D) TOPOLOGY: linear (ii) MOLECULE TYPE: nucleic acid (xi) SEQUENCE DESCRIPTION: SEQ ID NO: 2:

GGCTGATTGT CTTGACCA 18

(2) INFORMATION FOR SEQ ID NO: 3:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: nucleic acid (xi) SEQUENCE DESCRIPTION: SEQ ID NO: 3:

AGGAAGCCTC ACACTATCAT 20

(2) INFORMATION FOR SEQ ID NO: 4:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: nucleic acid (xi) SEQUENCE DESCRIPTION: SEQ ID NO: 4:

GTTGAAGACT ACGACGTTGA TAGG 24

(2) INFORMATION FOR SEQ ID NO: 5:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: nucleic acid (xi) SEQUENCE DESCRIPTION: SEQ ID NO: 5:

AATGTTTCAC TTCTGAGTTC G 21

(2) INFORMATION FOR SEQ ID NO: 6:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: nucleic acid (xi) SEQUENCE DESCRIPTION: SEQ ID NO: 6:

AACCACCTGA TACCATCTCG AACTCAGAA 29

(2) INFORMATION FOR SEQ ID NO: 7:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: nucleic acid -continued (xi) SEQUENCE DESCRIPTION: SEQ ID NO: 7:

ACGTGAAACG TATCGTGTAA ACTCTGACTC 30

(2) INFORMATION FOR SEQ ID NO: 8:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: nucleic acid (xi) SEQUENCE DESCRIPTION: SEQ ID NO: 8:

ATGCGAATAC AAGATGTAGG TTGGGC 26

(2) INFORMATION FOR SEQ ID NO: 9:

(i) SEQUENCE CHARACTERISTICS:
(A) LENGTH: 34 base pairs
(B) TYPE: nucleic acid
(C) STRANDEDNESS: single
(D) TOPOLOGY: linear (ii) MOLECULE TYPE: nucleic acid (xi) SEQUENCE DESCRIPTION: SEQ ID NO: 9:

ATGTAAATTG CTCAGACAAA TGAATACAGA GTTT 34

(2) INFORMATION FOR SEQ ID NO: 10:

(i) SEQUENCE CHARACTERISTICS:
(A) LENGTH: 31 base pairs
(B) TYPE: nucleic acid
(C) STRANDEDNESS: single
(D) TOPOLOGY: linear (ii) MOLECULE TYPE: nucleic acid (xi) SEQUENCE DESCRIPTION: SEQ ID NO: 10:

CCTGTTTTTA CAGAGCACTT AACAATGCTC T 31

(2) INFORMATION FOR SEQ ID NO: 11:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: nucleic acid (xi) SEQUENCE DESCRIPTION: SEQ ID NO: 11:

AATGCAAATA CAAGAAATTT AGGTTGGGC 29

(2) INFORMATION FOR SEQ ID NO: 12:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: nucleic acid (xi) SEQUENCE DESCRIPTION: SEQ ID NO: 12:

CTCTCTTTRT TTACCGGAAG TAACGCG 27

-continued (2) INFORMATION FOR SEQ ID NO: 13:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: nucleic acid (xi) SEQUENCE DESCRIPTION: SEQ ID NO: 13:

ATCAATACCT GGGGTAGGAC ACCTGC 26

(2) INFORMATION FOR SEQ ID NO: 14:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: nucleic acid (xi) SEQUENCE DESCRIPTION: SEQ ID NO: 14:

AACCCGGGTA AGACCGGAAA AACC 24

(2) INFORMATION FOR SEQ ID NO: 15:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: nucleic acid (xi) SEQUENCE DESCRIPTION: SEQ ID NO: 15:

GCAAAAATGA AAGACAAATG CGTTTGT 27

(2) INFORMATION FOR SEQ ID NO: 16:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: nucleic acid (xi) SEQUENCE DESCRIPTION: SEQ ID NO: 16:

TTAAACGCTT GTGAATCAAA CCCATTC 27

(2) INFORMATION FOR SEQ ID NO: 17:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: nucleic acid (xi) SEQUENCE DESCRIPTION: SEQ ID NO: 17:

TGATGAATGA ATATCCCCTA ACATGGG 27

(2) INFORMATION FOR SEQ ID NO: 18:

-continued (i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: nucleic acid (xi) SEQUENCE DESCRIPTION: SEQ ID NO: 18:

TGCTTGATAT AAGATATAAT ACCTCTTTAT TTACCTGAG 39

(2) INFORMATION FOR SEQ ID NO: 19:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: nucleic acid (xi) SEQUENCE DESCRIPTION: SEQ ID NO: 19:

GGCAATACTT TAATTAAAGG CATTAATGCC TA 32

(2) INFORMATION FOR SEQ ID NO: 20:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: nucleic acid (xi) SEQUENCE DESCRIPTION: SEQ ID NO: 20:

AGGCCTTGGG CTTGTTGATT GAA 23

(2) INFORMATION FOR SEQ ID NO: 21:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: nucleic acid (xi) SEQUENCE DESCRIPTION: SEQ ID NO: 21:

GTGCTGAATA TAAGATATAA TGTTACTCTC TTTATTTACC 40

(2) INFORMATION FOR SEQ ID NO: 22:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: nucleic acid (xi) SEQUENCE DESCRIPTION: SEQ ID NO: 22:

GTGTGCCCTG AAGAAGAAAC AGGGT 25

(2) INFORMATION FOR SEQ ID NO: 23:

(i) SEQUENCE CHARACTERISTICS:
(A) LENGTH: 28 base pairs
(B) TYPE: nucleic acid
(C) STRANDEDNESS: single -continued (D) TOPOLOGY: linear (ii) MOLECULE TYPE: nucleic acid (xi) SEQUENCE DESCRIPTION: SEQ ID NO: 23:

AATGTGTATA CAAGCTGTAG GTTGGCCA 28

(2) INFORMATION FOR SEQ ID NO: 24:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: nucleic acid (xi) SEQUENCE DESCRIPTION: SEQ ID NO: 24:

GTACGTACGA ATTAGAGATT GGGTCTAGGC 30

(2) INFORMATION FOR SEQ ID NO: 25:

(i) SEQUENCE CHARACTERISTICS:
(A) LENGTH: 31 base pairs
(B) TYPE: nucleic acid
(C) STRANDEDNESS: single
(D) TOPOLOGY: linear (ii) MOLECULE TYPE: nucleic acid (xi) SEQUENCE DESCRIPTION: SEQ ID NO: 25:

TTGTAGTAAT TGGCTGATTG TCTTGACCAT A 31

(2) INFORMATION FOR SEQ ID NO: 26:

(i) SEQUENCE CHARACTERISTICS:
(A) LENGTH: 336 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella pneumophila
(B) STRAIN: Philadelphia-1
(C) INDIVIDUAL ISOLATE: 01phila (xi) SEQUENCE DESCRIPTION: SEQ ID NO: 26:

GCCTCCCTCA AGATGAGTTT TCCCATGAAG CCCGTTGAAG ACTACGACGT TGATAGGCAA 60

GGTGTGGAAG CGCAGTAATG CGTGAAGCTA ACTTGTACTA ATTGGCTGAT TGTCTTGACC 120

ATATAATCTG AGTAACTTCA GAATRTGATA TTGATTTGTA TACCTGATAM GTATCGTGTA 180

AACTCTGACT CTTTACCAAA CCTGTGGCTT AATAAAGCAA TCAAAGCCTC AGGTAAACCA 240

GTTTTCCTGG CGACTATAGC GATTTGGAAC CACCTGATAC CATCTCGAAC TCAGAAGTGA 300

AACATTTCCG CGCCAATGAT AGTGTGAGGC TTCCTC 336

(2) INFORMATION FOR SEQ ID NO: 27:

(i) SEQUENCE CHARACTERISTICS:
(A) LENGTH: 336 base pairs
(B) TYPE: nucleic acid
(C) STRANDEDNESS: single
(D) TOPOLOGY: linear -continued (ii) MOLECULE TYPE: DNA (genomic)

(iii) HYPOTHETICAL: NO (vi) ORIGINAL SOURCE:
(A) ORGANISM: Legionella pneumophila
(B) STRAIN: Knoxville-1
(C) INDIVIDUAL ISOLATE: 02knox (xi) SEQUENCE DESCRIPTION: SEQ ID NO: 27:

```
GCCTCCCTCA AGATGAGTTT TCCCATGAAG CCCGTTGAAG ACTACGACGT TGATAGGCAA     60

GGTGTGGAAG CGCAGTAATG CGTGAAGCTA ACTTGTACTA ATTGGCTGAT TGTCTTGACC    120

ATATAATCTG AGTGACTTCA GAATGTGATA TTGATTTGTA TACGTGAAAC GTATCGTGTA    180

AACTCTGACT CTTTACCAAA CCTGTGGCTT AATATAGCAA TCAAAGCCTC AGGTAAACCA    240

GTTTTCCTGG CGACTATAGC GATTTGGAAC CACCTGATAC CATCTCGAAC TCAGAAGTGA    300

AACATTTCCG CGCCAATGAT AGTGTGAGGC TTCCTC                              336
```

(2) INFORMATION FOR SEQ ID NO: 28:

(i) SEQUENCE CHARACTERISTICS:
(A) LENGTH: 336 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella pneumophila
(B) STRAIN: Benidorm 030E
(C) INDIVIDUAL ISOLATE: 04beni (xi) SEQUENCE DESCRIPTION: SEQ ID NO: 28:

```
GCCTCCCTCA AGATGAGTTT TCCCATGAAG CCCGTTGAAG ACTACGACGT TGATAGGCAA     60

GGTGTGGAAG CGCAGTAATG CGTGAAGCTA ACTTGTACTA ATTGGCTGAT TGTCTTGACC    120

ATATAATCTG AGTGACTTCA GAATGTGATA TTGATTTGTA TACGTGAAAC GTATCGTGTA    180

AACTCTGACT CTTTACCAAA CCTGTGGCTT AATAATGCAA TCAAAGCCTC AGGTAAMCCA    240

GTTTTCCTGG CGACTATAGC GATTTGGAAC CACCTGATAC CATCTCGAAC TCAGAAGTGA    300

AACATTTCCG CGCCAATGAT AGTGTGAGGC TTCCTC                              336
```

(2) INFORMATION FOR SEQ ID NO: 29:

(i) SEQUENCE CHARACTERISTICS:
(A) LENGTH: 336 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella pneumophila
(B) STRAIN: France 5811
(C) INDIVIDUAL ISOLATE: 05fran (xi) SEQUENCE DESCRIPTION: SEQ ID NO: 29:

```
GCCTCCCTCA AGATGAGTTT TCCCATGAAG CCCGTTGAAG ACTACGACGT TGATAGGCAA     60

GGTGTGGAAG CGCAGTAATG CGTGAAGCTA ACTTGTACTA ATTGGCTGAT TGTCTTGACC    120
```

-continued

```
ATATAATCTG AGTRACTTCA GAATGTGATA TTGATTTGTA TACCTGAWAC GTATCGTGTA    180

AACTCTGACT CTTTACCAAM CCTGTGGCTT AATAWAGCAA TYAAAGCCTC AGGTAAACCA    240

GTTTTCCTGG CGACTATAGC GATTTGGAAC CACCTGATAC CATCTCGAAC TCAGAAGTGA    300

AACATTTCCG CGCCAATGAT AGTGTGAGGC TTCCTC                              336
```

(2) INFORMATION FOR SEQ ID NO: 30:

(i) SEQUENCE CHARACTERISTICS:
(A) LENGTH: 336 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella pneumophila
(B) STRAIN: OLDA
(C) INDIVIDUAL ISOLATE: 06olda (xi) SEQUENCE DESCRIPTION: SEQ ID NO: 30:

```
GCCTCCCTCA AGATGAGTTT TCCCATGNNN NNCGTTGAAG ACTACGACGT TGATAGGCAA     60

GGTGTGGAAG CGCAGTAATG CGTGAAGCTA ACTTGTACTA ATTGGCTGAT TGTCTTGACC    120

ATATAATCTG AGTGACTTCA GATTATGATA TTGATTTGTA TACGTGAAAC GTATCGTGTA    180

AACTCTGACT CTTTACCAAA CCTGTGGCTT AACAYAGCAA TCAAAGCCTC AGGTAATCCA    240

GTTTTCCTGG CGACTATAGC GATTTGGAAC CACCTGATAC CATCTCGAAC TCAGAAGTGA    300

AACATTTCCG CGCCAATGAT AGTGTGAGGC TTCCTC                              336
```

(2) INFORMATION FOR SEQ ID NO: 31:

(i) SEQUENCE CHARACTERISTICS:
(A) LENGTH: 335 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella pneumophila
(B) STRAIN: Oxford 4032E
(C) INDIVIDUAL ISOLATE: 07oxfo (xi) SEQUENCE DESCRIPTION: SEQ ID NO: 31:

```
GCCTCCCTCA AGATGAGTTT TCCCATGANN NNCGTTGAAG ACTACGACGT TGATAGGCAA     60

GGTGTGGAAG CGCAGTAATG CGTGAAGCTA ACTTGTACTA ATTGGCTGAT TGTCTTGACC    120

ATATAATCTG AGTGACTTCA GAATGTGATT TTGATTTGTA TACGTGAAAC GTATCGTGTA    180

AACTCTGACT CTTTACCAAA CSTGTGGCTT AATAATGCAA TCAAGCCTCA GGTAAACCAG    240

TTTTCCTGGC GACTATAGCG ATTTGGAACC ACCTGATACC ATCTCGAACT CAGAAGTGAA    300

ACATTTCCGC GCCAATGATA GTGTGAGGCT TCCTC                               335
```

(2) INFORMATION FOR SEQ ID NO: 32:

(i) SEQUENCE CHARACTERISTICS:
(A) LENGTH: 336 base pairs
(B) TYPE: nucleic acid
(C) STRANDEDNESS: single -continued (D) TOPOLOGY: linear (ii) MOLECULE TYPE: DNA (genomic)

(iii) HYPOTHETICAL: NO (vi) ORIGINAL SOURCE:
(A) ORGANISM: Legionella pneumophila
(B) STRAIN: Camperdown-1
(C) INDIVIDUAL ISOLATE: 08Camp (xi) SEQUENCE DESCRIPTION: SEQ ID NO: 32:

```
GCCTCCCTCA AGATGAGTTT TCCCATGAAG CCCGTTGAAG ACTACGACGT TGATAGGCAA     60

GGTGTGGAAG CGCAGTAATG CGTGAAGCTA ACTTGTACTA ATTGGCTGAT TGTCTTGACC    120

ATATAATCTG AGTGACTTCA GATTATGATA TTGATTTGTA TACGTGAAAC GTATCGTGTA    180

AACTCTGACT CTTTACCAAA CCTGTGGCTT AACATAGCAA TCAAAGCCTC AGGTAATCCA    240

GTTTTCCTGG CGACTATAGC GATTTGGAAC CACCTGATAC CATCTCGAAC TCAGAAGTGA    300

AACATTTCCG CGCCAATGAT AGTGTGAGGC TTCCTC                              336
```

(2) INFORMATION FOR SEQ ID NO: 33:

(i) SEQUENCE CHARACTERISTICS:
(A) LENGTH: 336 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella pneumophila
(B) STRAIN: Togus-1
(C) INDIVIDUAL ISOLATE: 09tog (xi) SEQUENCE DESCRIPTION: SEQ ID NO: 33:

```
GCCTCCCTCA AGATGAGTTT TCCCATGAAG CCCGTTGAAG ACTACGACGT TGATAGGCAA     60

GGTGTGGAAG CGCAGTAATG CGTGAAGCTA ACTTGTACTA ATTGGCTGAT TGTCTTGACC    120

ATATAATCTG AGTGACTTCA GAATGTGATA TTGATTTGTA TACCTGATAA GTATCGTGTA    180

AACTCTGACT CTTTACCAAA CCTGTGGCTT AATAAAGCAA TMAAAGCCTC AGGTAAMCCA    240

GTTTTCCTGG CGACTATAGC GATTTGGAAC CACCTGATAC CATCTCGAAC TCAGAAGTGA    300

AACATTTCCG CGCCAATGAT AGTGTGAGGC TTCCTC                              336
```

(2) INFORMATION FOR SEQ ID NO: 34:

(i) SEQUENCE CHARACTERISTICS:
(A) LENGTH: 336 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella pneumophila
(B) STRAIN: Bloomington-2
(C) INDIVIDUAL ISOLATE: 10Bloom (xi) SEQUENCE DESCRIPTION: SEQ ID NO: 34:

```
GCCTCCCTCA AGATGAGTTT TCCCATGANN NCCGTTGAAG ACTACGACGT TGATAGGCAA     60
```

-continued

```
GGTGTGGAAG CGCAGTAATG CGTGAAGCTA ACTTGTACTA ATTGGCTGAT TGTCTTGACC    120

ATATAATCTG AGTGACTTCA GAATGTGATA TTGATTTGTA TACGTGAAAC GTATCGTGTA    180

AACTCTGACT CTTTACCAAA CCTGTGGCTT AATATAGCAA TCAAAGCCTC AGGTAAACCA    240

GTTTTCCTGG CGACTATAGC GATTTGGAAC CACCTGATAC CATCTCGAAC TCAGAAGTGA    300

AACATTTCCG CGCCAATGAT AGTGTGAGGC TTCCTC                              336
```

(2) INFORMATION FOR SEQ ID NO: 35:

(i) SEQUENCE CHARACTERISTICS:
(A) LENGTH: 336 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella pneumophila
(B) STRAIN: Los Angeles-1
(C) INDIVIDUAL ISOLATE: 11sg41a (xi) SEQUENCE DESCRIPTION: SEQ ID NO: 35:

```
GCCTCCCTCA AGATGAGTTT TCCCATGNNN NNCGTTGAAG ACTACGACGT TGATAGGCAA     60

GGTGTGGAAG CGCAGTAATG CGTGAAGCTA ACTTGTACTA ATTGGCTGAT TGTCTTGACC    120

ATATAATCTG AGTGACTTCA GAATGTATAA TTGAATTGAA TACGTACAAC GCATCGTGTA    180

AACTCCGACT CTTTACCAAA CCTGTGGCTT AATAGTGTAA TCAAAGCCTC AGGTAAACCA    240

GTTTTCCTGG CGACTATAGC GATTTGGAAC CACCTGATAC CATCTCGAAC TCAGAAGTGA    300

AACATTTCCG CGCCAATGAT AGTGTGAGGC TTCCTC                              336
```

(2) INFORMATION FOR SEQ ID NO: 36:

(i) SEQUENCE CHARACTERISTICS:
(A) LENGTH: 336 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella pneumophila
(B) STRAIN: Portland
(C) INDIVIDUAL ISOLATE: 12sg4po (xi) SEQUENCE DESCRIPTION: SEQ ID NO: 36:

```
GCCTCCCTCA AGATGAGTTT TCCCATGAAG CCCGTTGAAG ACTACGACGT TGATAGGCAA     60

GGTGTGGAAG CGCAGTAATG CGTGAAGCTA ACTTGTACTA ATTGGCTGAT TGTCTTGACC    120

ATATAATCTG AGTAACTTCA GAATRTGATA TTGATTTGTA TACCTGATAM GTATCGTGTA    180

AACTCTGACT CTTTACCAAA CCTGTGGCTT AATAAAGCAA TCAAAGCCTC AGGTAAACCA    240

GTTTTCCTGG CGACTATAGC GATTTGGAAC CACCTGATAC CATCTCGAAC TCAGAAGTGA    300

AACATTTCCG CGCCAATGAT AGTGTGAGGC TTCCTC                              336
```

(2) INFORMATION FOR SEQ ID NO: 37:

(i) SEQUENCE CHARACTERISTICS:
(A) LENGTH: 336 base pairs

-continued (B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella pneumophila
(B) STRAIN: Dallas-1E
(C) INDIVIDUAL ISOLATE: 13sg5da (xi) SEQUENCE DESCRIPTION: SEQ ID NO: 37:

```
GCCTCCCTCA AGATGAGTTT TCCCATGAAG CCCGTTGAAG ACTACGACGT TGATAGGCAA     60

GGTGTGGAAG CGCAGTAATG YGTGAAGCTA ACTTGTACTA ATTGGCTGAT TGTCTTGACC    120

ATATAATCTG AGTGACTTCA GAATGTATAA TTGAATTGAA TACGTACAAC GCATCGTGTA    180

AACTCCGACT CTTTACCAAA CCTGTGGCTT AATAGTGTAA TCAAAGCCTC AGGTAAACCA    240

GTTTTCCTGG CGACTATAGC GATTTGGAAC CACCTGATAC CATCTCGAAC TCAGAAGTGA    300

AACATTTCCG CGCCAATGAT AGTGTGAGGC TTCCTC                              336
```

(2) INFORMATION FOR SEQ ID NO: 38:

(i) SEQUENCE CHARACTERISTICS:
(A) LENGTH: 336 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella pneumophila
(B) STRAIN: Cambridge-2
(C) INDIVIDUAL ISOLATE: 14sg5cam (xi) SEQUENCE DESCRIPTION: SEQ ID NO: 38:

```
GCCTCCCTCA AGATGAGTTT TCCCATGAAG CCCGTTGAAG ACTACGACGT TGATAGGCAA     60

GGTGTGGAAG CGCAGTAATG CGTGAAGCTA ACTTGTACTA ATTGGCTGAT TGTCTTGACC    120

ATATAATCTG AGTGACTTCA GAATGTGATA TTGATTTGTA TACGTGAAAC GTATCGTGTA    180

AACTCTGACT CTTTACCAAA CCTGTGGCTT AATACAGCAA TCAAAGCCTC AGGTAAACCA    240

GTTTTCCTGG CGACTATAGC GATTTGGAAC CACCTGATAC CATCTCGAAC TCAGAAGTGA    300

AACATTTCCG CGCCAATGAT AGTGTGAGGC TTCCTC                              336
```

(2) INFORMATION FOR SEQ ID NO: 39:

(i) SEQUENCE CHARACTERISTICS:
(A) LENGTH: 336 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella pneumophila
(B) STRAIN: Chicago-2
(C) INDIVIDUAL ISOLATE: 15sg6ch (xi) SEQUENCE DESCRIPTION: SEQ ID NO: 39:

-continued

GCCTCCCTCA AGATGAGTTT TCCCATGANN NNCGTTGAAG ACTACGACGT TGATAGGCAA 60

GGTGTGGAAG CGCAGTAATG CGTGAAGCTA ACTTGTACTA ATTGGCTGAT TGTCTTGACC 120

ATATAATCTG AGTAACTTCA GAATATGATA TTGATTTGTA TACCTGATAM GTATCGTGTA 180

AACTCTGACT CTTTACCAAA CCTGTGGCTT AATAAAGCAA TCAAAGCCTC AGGTAAACCA 240

GTTTTCCTGG CGACTATAGC GATTTGGAAC CACCTGATAC CATCTCGAAC TCAGAAGTGA 300

AACATTTCCG CGCCAATGAT AGTGTGAGGC TTCCTC 336

(2) INFORMATION FOR SEQ ID NO: 40:

(i) SEQUENCE CHARACTERISTICS:
(A) LENGTH: 336 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella pneumophila
(B) STRAIN: Chicago-8
(C) INDIVIDUAL ISOLATE: 16sg7

(xi) SEQUENCE DESCRIPTION: SEQ ID NO: 40:

GCCTCCCTCA AGATGAGTTT TCCCATGAAG CCCGTTGAAG ACTACGACGT TGATAGGCAA 60

GGTGTGGAAG CGCAGTAATG CGTGAAGCTA ACTTGTACTA ATTGGCTGAT TGTCTTGACC 120

ATATAATCTG AGTGACTTCA GAATGTGATA TTGATTTGTA TACGTGAAAC GTATCGTGTA 180

AACTCTGACT CTTTACCAAA CCTGTGGCTT AATATAGCAA TCAAAGCCTC AGGTAAACCA 240

GTTTTCCTGG CGACTATAGC GATTTGGAAC CACCTGATAC CATCTCGAAC TCAGAAGTGA 300

AACATTTCCG CGCCAATGAT AGTGTGAGGA CTCCTC 336

(2) INFORMATION FOR SEQ ID NO: 41:

(i) SEQUENCE CHARACTERISTICS:
(A) LENGTH: 336 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella pneumophila
(B) STRAIN: Concord-3
(C) INDIVIDUAL ISOLATE: 17sg8

(xi) SEQUENCE DESCRIPTION: SEQ ID NO: 41:

GCCTCCCTCA AGATGAGTTT TCCCATGAAG CCCGTTGAAG ACTACGACGT TGATAGGCAA 60

GGTGTGGAAG CGCAGTAATG CGTGAAGCTA ACTTGTACTA ATTGGCTGAT TGTCTTGACC 120

ATATAATCTG AGTGACTTCA GAATGTGATA TTGATTTGTA TACGTGAAAC GTATCGTGTA 180

AACTCTGACT CTTTACCAAA CCTGTGGCTT AATAAAGCAA GAAAAGCCTC AGGTAAACCA 240

GTTTTCCTGG CGACTATAGC GATTTGGAAC CACCTGATAC CATCTCGAAC TCAGAAGTGA 300

AACATTTCCG CGCCAATGAT AGTGTGAGGT CTCCTC 336

(2) INFORMATION FOR SEQ ID NO: 42:

-continued (i) SEQUENCE CHARACTERISTICS:
(A) LENGTH: 336 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella pneumophila
(B) STRAIN: IN-23-G1-C2
(C) INDIVIDUAL ISOLATE: 18sg9

(xi) SEQUENCE DESCRIPTION: SEQ ID NO: 42:

```
GCCTCCCTCA AGATGAGTTT TCCCATGANN NCCGTTGAAG ACTACGACGT TGATAGGCAA     60

GGTGTGGAAG CGCAGTAATG CGTGAAGCTA ACTTGTACTA ATTGGCTGAT TGTCTTGACC    120

ATATAATCTG AGTGACTTCA GATTATGATA TTGATTTGTA TACGTGAAAC GTATCGTGTA    180

AACTCTGACT CTTTACCAAA CCTGTGGCTT AACATAGCAA TCAAAGCCTC AGGTAATCCA    240

GTTTTCCTGG CGACTATAGC GATTTGGAAC CACCTGATAC CATCTCGAAC TCAGAAGTGA    300

AACATTTCCG CGCCAATGAT AGTGTGAGGC TTCCTC                              336
```

(2) INFORMATION FOR SEQ ID NO: 43:

(i) SEQUENCE CHARACTERISTICS:
(A) LENGTH: 336 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella pneumophila
(B) STRAIN: Leiden-1
(C) INDIVIDUAL ISOLATE: 19sg10

(xi) SEQUENCE DESCRIPTION: SEQ ID NO: 43:

```
GCCTCCCTCA AGATGAGTTT TCCCATGNNN NNCGTTGAAG ACTACGACGT TGATAGGCAA     60

GGTGTGGAAG CGCAGTAATG CGTGAAGCTA ACTTGTACTA ATTGGCTGAT TGTCTTGACC    120

ATATAATCTG AGTGACTTCA GAATGTGATA TTGATTTGTA TACGTGAAAC GTATCGTGTA    180

AACTCTGACT CTTTACCAAA CCTGTGGCTT AAYAYAGCAA TCAAAGCCTC AGGTAAACCA    240

GTTTTCCTGG CGACTATAGC GATTTGGAAC CACCTGATAC CATCTCGAAC TCAGAAGTGA    300

AACATTTCCG CGCCAATGAT AGTGTGAGGC TTCCTC                              336
```

(2) INFORMATION FOR SEQ ID NO: 44:

(i) SEQUENCE CHARACTERISTICS:
(A) LENGTH: 336 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella pneumophila
(B) STRAIN: 797-PA-H
(C) INDIVIDUAL ISOLATE: 20sg11

-continued (xi) SEQUENCE DESCRIPTION: SEQ ID NO: 44:

GCCTCCCTCA AGATGAGTTT TCCCATGAAG CCCGTTGAAG ACTACGACGT TGATAGGCAA 60

GGTGTGGAAG CGCAGTAATG CGTGAAGCTA ACTTGTACTA ATTGGCTGAT TGTCTTGACC 120

ATATAATCTG AGTGACTTCA GAATGTGATA TTGATTTGTA TACGTGAAAC GTATCGTGTA 180

AACTCTGACT CTTTACCAAA CCTGTGGCTT AATAATGCAA TCAAAGCCTC AGGTAAMCCA 240

GTTTTCCTGG CGMCTATAGC GATTTGGAAC CACCTGATAC CATCTCGAAC TCAGAAGTGA 300

AACATTTCCG CGCCAATGAT AGTGTGAGGC TTCCTC 336

(2) INFORMATION FOR SEQ ID NO: 45:

(i) SEQUENCE CHARACTERISTICS:
(A) LENGTH: 336 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella pneumophila
(B) STRAIN: 570-CO-H
(C) INDIVIDUAL ISOLATE: 21sg12

(xi) SEQUENCE DESCRIPTION: SEQ ID NO: 45:

GCCTCCCTCA AGATGAGTTT TCCCATGNNN NNCGNNGAAG ACTACGACGT TGATAGGCAA 60

GGTGTGGAAG CGCAGTAATG CGTGAAGCTA ACTTGTACTA ATTGGCTGAT TGTCTTGACC 120

ATATAATCTG AGTAACTTCA GAATRTGATA TTGATTTGTA TACCTGATAM GTATCGTGTA 180

AACTCTGACT CTTTACCAAA CCTGTGGCTT AATAAAGCAA TCAAAGCCTC AGGTAAACCA 240

GTTTTCCTGG CGACTATAGC GATTTGGAAC CACCTGATAC CATCTCGAAC TCAGAAGTGA 300

AACATTTCCG CGCCAATGAT AGTGTGAGGC TTCCTC 336

(2) INFORMATION FOR SEQ ID NO: 46:

(i) SEQUENCE CHARACTERISTICS:
(A) LENGTH: 336 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella pneumophila
(B) STRAIN: 82-A-3105
(C) INDIVIDUAL ISOLATE: 22sg13

(xi) SEQUENCE DESCRIPTION: SEQ ID NO: 46:

GCCTCCCTCA AGATGAGTTT TCCCATGAAG CCCGTTGAAG ACTACGACGT TGATAGGCAA 60

GGTGTGGAAG CGCAGTAATG CGTGAAGCTA ACTTGTACTA ATTGGCTGAT TGTCTTGACC 120

ATATAATCTG AGTGACTTCA GAATGTGATA TTGATTTGTA TACGTGAAAC GTATCGTGTA 180

AACTCTGACT CTTTACCAAA CCTGTGGCTT AATACAGCAA TCAAAGCCTC AGGTAAACCA 240

GTTTTCCTGG CGACTATAGC GATTTGGAAC CACCTGATAC CATCTCGAAC TCAGAAGTGA 300

AACATTTCCG CGCCAATGAT AGTGTGAGGC TTCCTC 336

-continued (2) INFORMATION FOR SEQ ID NO: 47:

(i) SEQUENCE CHARACTERISTICS:
(A) LENGTH: 336 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella pneumophila
(B) STRAIN: 1169-MN-H
(C) INDIVIDUAL ISOLATE: 23sg14

(xi) SEQUENCE DESCRIPTION: SEQ ID NO: 47:

GCCTCCCTCA AGATGAGTTT TCCCATGAAG CCCGTTGAAG ACTACGACGT TGATAGGCAA 60

GGTGTGGAAG CGCAGTAATG CGTGAAGCTA ACTTGTACTA ATTGGCTGAT TGTCTTGACC 120

ATATAATCTG AGTGACTTCA GAATGTGATA TTGATTTGTA TACGTGAAAC GTATCGTGTA 180

AACTCTGACT CTTTACCAAA CCTGTGGCTT AAYAYAGCAA TCAAAGCCTC AGGTAAACCA 240

GTTTTCCTGG CGACTATAGC GATTTGGAAC CACCTGATAC CATCTCGAAC TCAGAAGTGA 300

AACATTTCCG CGCCAATGAT AGTGTGAGGC TTCCTC 336

(2) INFORMATION FOR SEQ ID NO: 48:

(i) SEQUENCE CHARACTERISTICS:
(A) LENGTH: 374 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella anisa
(B) STRAIN: WA-316-C2
(C) INDIVIDUAL ISOLATE: 24ani (xi) SEQUENCE DESCRIPTION: SEQ ID NO: 48:

GAAGCCTCCC TCAAGATGAG TTTTCCCATG AAGCCCGTTG AAGACTACGA CGTTGATAGG 60

CAAGGTGTGG AAGCACAGTA ATGTGTGAAG CTAACTTGTA CTAATTGGCT GATTGTCTTG 120

ACCATATAAT CTGAGTTACT TCAGATTGTG AATGCGAATA CAAGATGTAG GTTGGGCCAA 180

GGCTCAACCT ACGCAGAACT ACTTGAAACA AAGTGTGAAC TTCTTTATTT ACCTAATGCT 240

TGATTGAGGT ATAATGCCTT ACAATCAATG CAAAACCAGT TTTCCTGGCG ACCATAGCGG 300

TTTGGAACCA CCTGAATCCA TCTCGAACTC AGAAGTGAAA CGAACCCGCG CCAATGATAG 360

TGTGAGGTTT CCTC 374

(2) INFORMATION FOR SEQ ID NO: 49:

(i) SEQUENCE CHARACTERISTICS:
(A) LENGTH: 350 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:

-continued (A) ORGANISM: Legionella brunensis (xi) SEQUENCE DESCRIPTION: SEQ ID NO: 49:

GCCTCCCTCA AGATGAGTTT TCCCATGAAG CCCGTTGAAG ACTACGACGT TGATAGGCGA 60

GGTGTGGAAG CGCAGTAATG TGTGAAGCTA ACTCGTACTA ATTGGCTGAT TGTCTTGACC 120

ATATAACCTG AATGACTTCG GGTTATGATA GAAGATGATA GATTATGCCG TAAGGCACTT 180

GTGTTAACCC TTTTTTACTT TACCAGCCTG TTTTTACAGA GCACTTAACA ATGCTCTTTA 240

TCAACAGGAC AACAGTTTTC CTGGCGACCA TAGCGGTTTG GAACCACCTG ACTCCATCTC 300

GAACTCAGTA GTGAAACAGA CCAGCGCCGA TGATAGTGTG AGGCTTCCTC 350

(2) INFORMATION FOR SEQ ID NO: 50:

(i) SEQUENCE CHARACTERISTICS:
(A) LENGTH: 317 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella cincinnatiensis
(B) STRAIN: 72-OH-H
(C) INDIVIDUAL ISOLATE: 29cin (xi) SEQUENCE DESCRIPTION: SEQ ID NO: 50:

GCCTCCCTCA AGCTGAGTTT TCCCTTGAAG CCCGTTGAAG ACTACGACGT TGATAGGCAA 60

GGTGTGGAAG CGTAGTAATG CGTGAAGCTA ACTTGTACTA ATTGGCTGAT TGTCTTGACC 120

ATATAATCTG AGTTACTTCA GAGTGAAACA GAATATAAGT GACACCATGA CTCTCTTTRT 180

TTACCGGAAG TAACGCGCTC CAAGGCGCGC TACTCAAAAC AGTTTTCCTG GCGACCATAG 240

CGGTTTGGAA CCACCTGATT CCATCTCGAA CTCAGTAGTG AAACGAACAT GCGCCAATGA 300

TAGTGTGAGG TTTCCTC 317

(2) INFORMATION FOR SEQ ID NO: 51:

(i) SEQUENCE CHARACTERISTICS:
(A) LENGTH: 359 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella dumoffii
(B) STRAIN: NY-23
(C) INDIVIDUAL ISOLATE: 31DUMO (xi) SEQUENCE DESCRIPTION: SEQ ID NO: 51:

GCCTCCCTCA AGATGAGTTT TCCCATGAAG CCCGTTGGAG ACTACGACGT TGATAGGCAA 60

GGTGTGGAAG CGCAGTAATG CGTGCAGCTA ACTTGTACTA ATTGGCTGAT TGTCTTGACC 120

ATATAATCTG AGTTACTTCA GATGAACTGA ATCAATACCT GGGGTAGGAC ACCTGCCCCG 180

AAATAAATAC AAAATAGTGT GTCCTCTTTA TTTACCTCGT GCATGATTCG GGTATAATAT 240

GCCCAATTGA TCATGTCAAA CCAGTTTTCC TGGCGACCAT AGCGGTTTGG AACCACCTGA 300

ATCCATCTCG AACTCAGAAG TGAAACGAAC ATGCGCCAAT GATAGTGTGA GGCTTCCTC 359

-continued (2) INFORMATION FOR SEQ ID NO: 52:

(i) SEQUENCE CHARACTERISTICS:
(A) LENGTH: 362 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella cherrii
(B) STRAIN: ORW
(C) INDIVIDUAL ISOLATE: 30che (xi) SEQUENCE DESCRIPTION: SEQ ID NO: 52:

GCCTCCCTCA AGATGAGTTT TCCCATGAAG CCCGTTGAAG ACTACGACGT TGATAGGCAA 60

GGTGTGGAAG CACAGTAATG TGTGCAGCTA ACTTGTACTA ATTGGCTGAT TGTCTTGACC 120

ATATAATCTG AATTACTTCA GATTAACTGA ATGCAAATAC AAGAAATTTA GGTTGGGCCA 180

CGGCCCAATC TGCAAAAAAA ATGTGTACTC TTTATTTACC TAACGCATGA TTCGGGTATA 240

ATGCGCCCAT TAATCATGTT AAACCAGTTT TCCTGGCGAC CATAGCGGTT TGGAACCACC 300

TGACTCCATC TCGAACTCAG AAGTGAAACG AACCCGCGCC AATGATAGTG TGAGGTTTCC 360

TC 362

(2) INFORMATION FOR SEQ ID NO: 53:

(i) SEQUENCE CHARACTERISTICS:
(A) LENGTH: 325 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella erythra
(B) STRAIN: SE-32A-C8
(C) INDIVIDUAL ISOLATE: 32ERY (xi) SEQUENCE DESCRIPTION: SEQ ID NO: 53:

GCCTCCCTCA AGATGAGTTT TCCCATGAAG CCCGTTGAAG ACTACGACGT TGATAGGCGA 60

GGTGTGGAAG CGTAGTAATG CGTGAAGCTA ACTCGTACTA ATTGGCTGAT TGTCTTGACT 120

ATATAACCTG ATGCGCTTCA GGTTATATGG ATAACATGAA TGTGACTCTA TTTTTTACCG 180

GCCTCGTGGC CAACCCGGGT AAGACCGGAA AAACCATGAT GCTTAAACCG TTTTCCTGGC 240

GACCATAGCA GTTTGGAACC ACCTGAATCC ATCTCGAACT CAGAAGTGAA ACAGACTCGC 300

GCCGATGATA GTGTGAGGCT TCCTC 325

(2) INFORMATION FOR SEQ ID NO: 54:

(i) SEQUENCE CHARACTERISTICS:
(A) LENGTH: 342 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO

-continued (vi) ORIGINAL SOURCE:
(A) ORGANISM: Legionella feeleii
(B) STRAIN: WO-44C
(C) INDIVIDUAL ISOLATE: 33feel (xi) SEQUENCE DESCRIPTION: SEQ ID NO: 54:

```
GCCTCCCTCA AGATGAGTTT TCCCATGAAG CCCGTTGAAG ACTACGACGT TGATAGGCGA     60

GGTGTGGAAG CGCAGTAATG CGTGAAGCTA ACTCGTACTA ATTGGCTGAT TGTCTTGACC    120

ATATAACCTG AATTGCTTTG AGGTTATAGG CAAAAATGAA AGACAAATGC GTTTGTGTTA    180

CCTCATAATC TTTACCGGCC TGCTGGCTGA GCACTTAACC CTGCTTTATC CAGAACAGGC    240

AAACCCGTTT TCCTGGCGAC CATAGCGGTT TGGAACCACC TGACTCCATC TCGAACTCAG    300

AAGTGAAACA AACCCGCGCC GATGATAGTG TGGAGTTTCT CC                       342
```

(2) INFORMATION FOR SEQ ID NO: 55:

(i) SEQUENCE CHARACTERISTICS:
(A) LENGTH: 349 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella feeleii
(B) STRAIN: 691-WI-H
(C) INDIVIDUAL ISOLATE: 34feel (xi) SEQUENCE DESCRIPTION: SEQ ID NO: 55:

```
GCGGGAAGCC TCCCTCAAGA TGAGTTTTCC CATGAAGCCC GTTGAAGACT ACGACGTTGA     60

TAGGCGAGGT GTGGAAGCGC AGTAATGCGT GAAGCTAACT CGTACTAATT GGCTGATTGT    120

CTTGACCATA TAACCTGAAT TGCTTTGAGG TTATAGGCAA AAATGAAAGA CAAATGCGTT    180

TGTGTTACCT CATAATCTTT ACCGGCCTGC TGGCTGAGCA CTTAAACCTG CTTTATCCAG    240

AACAGGCAAA CCCGTTTTCC TGGCGACCAT AGCGGTTTGG AACCACCTGA CTCCATCTCG    300

AACTCAGAAG TGAAACAAAC CCGCGCCGAT GATAGTGTGG AGTTTCTCC                349
```

(2) INFORMATION FOR SEQ ID NO: 56:

(i) SEQUENCE CHARACTERISTICS:
(A) LENGTH: 321 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella israelensis
(B) STRAIN: Bercovier-4
(C) INDIVIDUAL ISOLATE: 36isr (xi) SEQUENCE DESCRIPTION: SEQ ID NO: 56:

```
GCCTTCCTCA AGATGAGTTT TCCCTTGAAG CCCGTTGAAG ACGACGACGT TGATAGGCGA     60

GGTGTGGAAG CGCAGTAATG TGTGAAGCTA ACTCGTACTA ATTGGCTGAT TGTCTTGACC    120

ATATATCCTG AAATCATTCA GGGCATGATA CAAAATGAGT TTAAACGCTT GTGAATCAAA    180

CCCATTCAAT CTTTACCTTC TGCCTTCAAT AAGGCAGAAT AACCCGTTTT CCTGGCGACC    240
```

-continued

ATAGCTGTTT GGTACCACCT GATACCTTTC CGAACTCAGT AGTGAAACAA ACACGCGCTG 300

ATGATAGTGT GGGGTCTCCC C 321

(2) INFORMATION FOR SEQ ID NO: 57:

(i) SEQUENCE CHARACTERISTICS:
(A) LENGTH: 348 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella jordanis
(B) STRAIN: BL-540
(C) INDIVIDUAL ISOLATE: 38jor (xi) SEQUENCE DESCRIPTION: SEQ ID NO: 57:

GCCTCCCTCA AGATGAGTTT TCCCATGAAG CCCGTTGAAG ACTACGACGT TGATAGGCGA 60

GGTGTGGAAG CGCAGTAATG TGTGAAGCTA ACTCGTACTA ATTGGCTGAT TGTCTTGACC 120

ATATAACCTG AATGGCTTTT ATGTGGCAAG TCAAAGACAA GGCTTGGCAA GCTTGTGTTG 180

CCCTAATATT TATCTTTACC AGCCTGATGA ATGAATATCC CCTAACATGG GTATTTGCTC 240

AGCAGGACAA CGTTTTTCCT GGCGACCATA GCGGTTTGGA ACCACCTGAC TCCATCTCGA 300

ACTCAGAAGT GAAACAGACC AGCGCCGATG ATAGTGTGAG GCTTCCTC 348

(2) INFORMATION FOR SEQ ID NO: 58:

(i) SEQUENCE CHARACTERISTICS:
(A) LENGTH: 312 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella longbeachae sero.1
(B) STRAIN: Long Beach-4
(C) INDIVIDUAL ISOLATE: 39long1

(xi) SEQUENCE DESCRIPTION: SEQ ID NO: 58:

GCCTCCCTCA AGATGAGTTT TCCCTTGAAG CCCGTTGAAG ACTACGACGT TGATAGGCAA 60

GGTGTGGAAG CGTAGTAATG CGTGAAGCTA ACTTGTACTA ATTGGCTGAT TGTCTTGACC 120

ATATAATCTG AGTTACTTTA GATTATGCTT GATATAAGAT ATAATACCTC TTTATTTACC 180

TGAGTATCAT GCCAATAATG CGCGATACTC AAAACAGTTT TCCTGGCGAC TATAGCGGTT 240

TGGAACCACC TGAATCCATC TCGAACTCAG AAGTGAAACG TACATGCGCC AATGATAGTG 300

TGAGGCTTCC TC 312

(2) INFORMATION FOR SEQ ID NO: 59:

(i) SEQUENCE CHARACTERISTICS:
(A) LENGTH: 312 base pairs
(B) TYPE: nucleic acid
(C) STRANDEDNESS: single
(D) TOPOLOGY: linear (ii) MOLECULE TYPE: DNA (genomic)

-continued (iii) HYPOTHETICAL: NO (vi) ORIGINAL SOURCE:
(A) ORGANISM: Legionella lonbeachae sero.2
(B) STRAIN: Tucker-1
(C) INDIVIDUAL ISOLATE: 40long2

(xi) SEQUENCE DESCRIPTION: SEQ ID NO: 59:

```
GCCTCCCTCA AGATGAGTTT TCCCTTGAAG CCCGTTGAAG ACTACGACGT TGATAGGCAA     60

GGTGTGGAAG CGTAGTAATG CGTGAAGCTA ACTTGTACTA ATTGGCTGAT TGTCTTGACC    120

ATATAATCTG AGTTACTTTA GATTATGCTT GATATAAGAT ATAATACCTC TTTATTTACC    180

TGAGTATCAT GCCAATAATG CGCGATACTC AAAACAGTTT TCCTGGCGAC TATAGCGGTT    240

TGGAACCACC TGAATCCATC TCGAACTCAG AAGTGAAACG AACATGCGCC AATGATAGTG    300

TGAGGCTTCC TC                                                        312
```

(2) INFORMATION FOR SEQ ID NO: 60:

(i) SEQUENCE CHARACTERISTICS:
(A) LENGTH: 354 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella machearchernii
(B) STRAIN: PX-1-G2-E2
(C) INDIVIDUAL ISOLATE: 41mac (xi) SEQUENCE DESCRIPTION: SEQ ID NO: 60:

```
GCCTCCCTCA AGATGAGTTT TCCCATGAAG CCCGTTGGAG ACTACGACGT TGATAGGCGA     60

GGTGTGGAAG CACAGTAATG TGTGTAGCTA ACTCGTACTA ATTGGCTGAT TGTCTTGACC    120

ATATAACCTG AGCTGCTTTT AGGTTGAAGA GTAAGTGATA AGGCAATACT TTAATTAAAG    180

GCATTAATGC CTAAGCGTTT GTGTTAACCT CTAACCCCTT TACCAAGCTG ATTGGCGAAT    240

AGGCCAATCG GTAAACCAGT TTTCCTGGCG ACCATAGCGG TTTGGAACCA CCTGAATCCA    300

TCTCGAACTC AGAAGTGAAA CAGACCTGCG CCAATGATAG TGTGGGGCTT CCCC          354
```

(2) INFORMATION FOR SEQ ID NO: 61:

(i) SEQUENCE CHARACTERISTICS:
(A) LENGTH: 374 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella micdadei
(B) STRAIN: Tatlock
(C) INDIVIDUAL ISOLATE: 42micd (xi) SEQUENCE DESCRIPTION: SEQ ID NO: 61:

```
GAAGCCTCCC TCAAGATGAG TTTTCCCATG AAGCCCGTTG AAGACTACGA CGTTGATAGG     60

CGAGGTGTGG AAGCACAGTA ATGTGTGTAG CTAACTCGTA CTAATTGGCT GATTGTCTTG    120

ACCATATAAC CTGAACTGCC TTTAGGTTAT GAGTGAAGAA GCAAGGCAAT ATTGAATGAC    180
```

-continued

AGGGCAATGT AAATTGCTCA GACAAATGAA TACAGAGTTT GTGTTAACCT CTATCCACTT 240

TACCAAGCTG ATTGGTTAAT AGCCCAATCG GTAAACCAGG TTTCCTGGCG ACTATAGCGG 300

TTTGGAACCA CCTGATCCCA TCTCGAACTC AGAAGTGAAA CATACCTGCG CCAATGATAG 360

TGTGGGGCTT CCCC 374

(2) INFORMATION FOR SEQ ID NO: 62:

(i) SEQUENCE CHARACTERISTICS:
(A) LENGTH: 340 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella moravica
(B) STRAIN: 316-36
(C) INDIVIDUAL ISOLATE: 43monr (xi) SEQUENCE DESCRIPTION: SEQ ID NO: 62:

GCCTCCCTCA AGATGAGTTT TCCCATGAAG CCCGTTGAAG ACTACGACGT TGATAGGCAA 60

GGTGTGGAAG CGCAGTAATG TGTGAAGCTA ACTTGTACTA ATTGGCTGAT TGTCTTGACC 120

ATATAATCTG AGTTACTTCG GGTTATAGAA GTAGACGATA AAATAGAGTA GAATGTGTTA 180

CCTCGAATCT TTACCAGGCC TTGGGCTTGT TGATTGAACN CAATCATCAA TCTGAAGGTA 240

AACAGTTTTC CTGGCGACAA TAGCGGTTTG GAACCACCTG ATCCCATCTC GAACTCAGAA 300

GTGAAACGAA CATGCGCCGA TGATAGTGTG AGGCTTCCTC 340

(2) INFORMATION FOR SEQ ID NO: 63:

(i) SEQUENCE CHARACTERISTICS:
(A) LENGTH: 302 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella oakridgensis
(B) STRAIN: OR-10
(C) INDIVIDUAL ISOLATE: 44oak (xi) SEQUENCE DESCRIPTION: SEQ ID NO: 63:

AGCCTCCCTC GAGATGAGTT TTCCCATGAA GCCCGTTGAA GACGACGACG TTGATAGGCG 60

AGGTGTGGAA GCGTAGTAAT ACGTGAAGCT AACTCGTACT AATTGGCTGA TTGTCTTGAC 120

CATATAACCT GAGTTGATTC AGGTTAACGC ATGCGTTTGT GTATGCCTCA ATCTTTACCA 180

CTTGGAAGCG TAAGCTTCCA ATACCGTTTT TCCTGGCGAC CATAGCCGTT TGGAACCACC 240

TGATACCATC CCGAACTCAG AAGTGAAACG AACGCGCGCC AATGATAGTG TGGGGCTTCC 300

CC 302

(2) INFORMATION FOR SEQ ID NO: 64:

(i) SEQUENCE CHARACTERISTICS:
(A) LENGTH: 323 base pairs
(B) TYPE: nucleic acid

-continued (C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella rubrilucens
(B) STRAIN: WA-270A-C2
(C) INDIVIDUAL ISOLATE: 45rub (xi) SEQUENCE DESCRIPTION: SEQ ID NO: 64:

```
GCCTCCCTCA AGATGAGTTT TCCCATGAAG CCCGTTGAAG ACTACGACGT TGATAGGCGA     60

GGTGTGGAAG CGCAGTAATG CGTGAAGCTA ACTCGTACTA ATTGGCTGAT TGTCTTGACC    120

ATATAACCTG ATACGCTTCA GGTTATAGCA ATAACATGAA TGTGACTCTA TTYTTTACCG    180

GCCTCATGGC CAGCGGTTAA CACCGTTGCC ACCATGACGC TTAAACCGTT TTCCTGGCGA    240

CCATAGCAGT CTGGAACCAC CTGAATCCAT CTCGAACTCA GAAGTGAAAC AGACTCGCGC    300

CGATGATAGT GTGAGGTTTC CTC                                            323
```

(2) INFORMATION FOR SEQ ID NO: 65:

(i) SEQUENCE CHARACTERISTICS:
(A) LENGTH: 316 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella sainthelensis
(B) STRAIN: Mt.St. Helens-4
(C) INDIVIDUAL ISOLATE: 46saint (xi) SEQUENCE DESCRIPTION: SEQ ID NO: 65:

```
GCCTCCCTCA AGATGAGTTT TCCCTTGAAG CCCGTTGAAG ACTACGACGT TGATAGGCAA     60

GGTGTGGAAG CGTAGTAATG CGTGAAGCTA ACTTGTACTA ATTGGCTGAT TGTCTTGACC    120

ATATAATCTG AGTTACTTCA GATTGTGCTG AATATAAGAT ATAATGTTAC TCTCTTTATT    180

TACCTGAGTA TCATGCGGCT AATGCACGAT ACTCAAAACA GTTTTCCTGG CGACCATAGC    240

GGTTTGGTAC CACCTGATTC CATCTCGAAC TCAGAAGTGA AACGAACATG CGCCAATGAT    300

AGTGTGAGGC TTCCTC                                                    316
```

(2) INFORMATION FOR SEQ ID NO: 66:

(i) SEQUENCE CHARACTERISTICS:
(A) LENGTH: 350 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella spiritensis
(B) STRAIN: Mt. St. Helens-9
(C) INDIVIDUAL ISOLATE: 47spir (xi) SEQUENCE DESCRIPTION: SEQ ID NO: 66:

```
GCCTCCCTCA AGATGAGTTT TCCCATGAAG CCCGTTGAAG ACTACGACGT TGATAGGCGA     60
```

-continued

```
GGTGTGGAAG CGTAGTAATG CGTGAAGCTM ACTCGTACTA ATTGGCTGAT TGTCTTGACC    120

ATATAACCTG AATGACTTCG GGTTATTGAT ACGAAAGATA CGAAAAGAAG CAAGAACGAT    180

TGTGTTACCG AATATCTCTT TACCAGCCTG TGGTGTGCCC TGAAGAAGAA ACAGGGTTAC    240

GACTCAGGAT AACCGTTTTC CTGGCGATTA TAGCCGTGTG GAACCACCTG ATTCCATCTC    300

GAACTCAGAA GTGAAACGCA CGTACGCCGA TGATAGTGTG GGGTCTCCCC               350
```

(2) INFORMATION FOR SEQ ID NO: 67:

(i) SEQUENCE CHARACTERISTICS:
(A) LENGTH: 360 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella steigerwaltii
(B) STRAIN: SC-18-C9
(C) INDIVIDUAL ISOLATE: 48steig (xi) SEQUENCE DESCRIPTION: SEQ ID NO: 67:

```
GCCTCCCTCA AGATGAGTTT TCCCATGAAG CCCGTTGAAG ACTACGACGT TGATAGGCAA     60

GGTGTGGAAG CGCAGTAATG TGTGAAGCTA ACTTGTACTA ATTGGCTGAT TGTCTTGACC    120

ATATAATCTG AATTACTTCA GAGTGACTGA ATGTGTATAC AAGCTGTAGG TTGGCCAAGG    180

CACAACCTAC AGAAATAAAT TGTGAACCCT TTATTTACCT AATGCATGAT TCGGGTATAA    240

TACGCCCAAC ATCATGTAAA ACCAGTTTTC CTGGCGACCA TAGCGGTTTG GAACCACCTG    300

ACTCCATCTC GAACTCAGAA GTGAAACAGA CCCGCGCCAA TGATAGTGTG AGGTTTCCTC    360
```

(2) INFORMATION FOR SEQ ID NO: 68:

(i) SEQUENCE CHARACTERISTICS:
(A) LENGTH: 366 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(A) ORGANISM: Legionella wadsworthii
(B) STRAIN: 81-716A
(C) INDIVIDUAL ISOLATE: 49wad (xi) SEQUENCE DESCRIPTION: SEQ ID NO: 68:

```
GCCTCCCTCA AGATGAGTTT TCCCTTGAAG CCCGTTGAAG ACTACGACGT TGATAGGCAA     60

GGTGTGGAAG CGCAGTAATG TGTGAAGCTA ACTTGTACTA ATTGGCTGAT TGTCTTGACC    120

ATATAATCTG AGTTACTTCA GGTTAACTGA TAAGTACGTA CGAATTAGAG ATTGGGTCTA    180

GGCCCAATCT AAAAAAAATA AAAAAATGTG AACCTTTTTA TTTACCTATA GCATGATTAG    240

GGTATAATAC GCCCAATTCA TGCGAAACCA GTTTTCCTGG CGACAATAGC GGCTTGGAAC    300

CACCTGATCC CATCTCGAAC TCAGAAGTGA AACGAGCATG CGCCAATGAT AGTGTGAGGT    360

CTCCTC                                                               366
```